US009969675B2

(12) United States Patent
Fukuda et al.

(10) Patent No.: US 9,969,675 B2
(45) Date of Patent: May 15, 2018

(54) METHOD FOR PRODUCING TRANS-BIS(AMINOMETHYL)CYCLOHEXANE, METHOD FOR PRODUCING BIS(ISOCYANATOMETHYL)CYCLOHEXANE, BIS(ISOCYANATOMETHYL)CYCLOHEXANE, POLYISOCYANATE COMPOSITION, AND POLYURETHANE RESIN

(71) Applicant: MITSUI CHEMICALS, INC., Tokyo (JP)

(72) Inventors: Takeshi Fukuda, Kurume (JP); Kazuhiro Kosumi, Omuta (JP); Jun Takahashi, Omuta (JP); Keita Takuno, Mobara (JP); Ryo Shinagawa, Omuta (JP); Masashi Shimamoto, Tamana (JP); Gran Martinez Alejandro, Chiba (JP); Satoshi Yamasaki, Chiba (JP); Goro Kuwamura, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days. days.

(21) Appl. No.: 14/908,875

(22) PCT Filed: Jul. 25, 2014

(86) PCT No.: PCT/JP2014/069695
§ 371 (c)(1),
(2) Date: Jan. 29, 2016

(87) PCT Pub. No.: WO2015/016148
PCT Pub. Date: Feb. 5, 2015

(65) Prior Publication Data
US 2016/0207875 A1    Jul. 21, 2016

(30) Foreign Application Priority Data

Aug. 1, 2013  (JP) ................................ 2013-160592

(51) Int. Cl.
| | | |
|---|---|---|
| C07C 209/48 | (2006.01) | |
| C07C 265/04 | (2006.01) | |
| C07C 265/14 | (2006.01) | |
| C07C 263/10 | (2006.01) | |
| C07C 253/30 | (2006.01) | |
| C07C 211/18 | (2006.01) | |
| C07C 255/46 | (2006.01) | |
| C08G 18/78 | (2006.01) | |
| C08G 18/75 | (2006.01) | |

(52) U.S. Cl.
CPC .......... C07C 209/48 (2013.01); C07C 253/30 (2013.01); C07C 263/10 (2013.01); C07C 265/04 (2013.01); C07C 265/14 (2013.01); C08G 18/757 (2013.01); C08G 18/7837 (2013.01)

(58) Field of Classification Search
CPC ... C07C 209/48; C07C 265/04; C07C 263/10; C07C 253/30; C07C 265/14; C07C 211/18; C07C 255/46; C08G 18/7837
See application file for complete search history.

(56) References Cited

U.S. PATENT DOCUMENTS

| | | | |
|---|---|---|---|
| 3,251,874 A * | 5/1966 | Strickland | C07C 211/18 558/356 |
| 3,344,164 A | 9/1967 | Seaton | |
| 8,722,752 B2 * | 5/2014 | Kuwamura | B29C 41/18 521/170 |
| 9,475,903 B2 * | 10/2016 | Yamasaki | C08G 18/12 |
| 9,477,012 B2 * | 10/2016 | Yamasaki | C08G 18/12 |
| 2009/0000516 A1 | 1/2009 | Jokisch | |
| 2010/0216905 A1 | 8/2010 | Kuwamura | |
| 2012/0130002 A1 | 5/2012 | Tang | |
| 2013/0197269 A1 | 8/2013 | Kiyono | |
| 2013/0324631 A1 | 12/2013 | Kuwamura | |
| 2015/0291758 A1 | 10/2015 | Kuwamura | |

FOREIGN PATENT DOCUMENTS

| | | |
|---|---|---|
| EP | 2204395 | 7/2010 |
| JP | 11335335 A2 | 12/1999 |
| JP | 2009138182 A2 | 6/2009 |
| JP | 2009523151 | 6/2009 |
| JP | 2009161727 A2 | 7/2009 |
| JP | 2011006382 A2 | 1/2011 |
| JP | 2011111424 A2 | 6/2011 |

(Continued)

OTHER PUBLICATIONS

International Preliminary Report on Patentability dated Oct. 28, 2014 filed in PCT/JP2014/069695, total 20 pages.

(Continued)

*Primary Examiner* — Rabon Sergent
(74) *Attorney, Agent, or Firm* — Rankin, Hill & Clark LLP

(57) ABSTRACT

A method for producing trans-bis(aminomethyl)cyclohexane includes a trans-isomerization step in which cis-dicyanocyclohexane is isomerized into trans-dicyanocyclohexane by heating dicyanocyclohexane containing cis-dicyanocyclohexane in the presence of a tar component produced by distillation of dicyanocyclohexane; and an aminomethylation step in which trans-dicyanocyclohexane produced by the trans-isomerization step is allowed to contact with hydrogen to produce trans-bis(aminomethyl)cyclohexane.

8 Claims, 2 Drawing Sheets

(56) References Cited

FOREIGN PATENT DOCUMENTS

| | | |
|---|---|---|
| JP | 2011252083 A2 | 12/2011 |
| JP | 2012111935 A2 | 6/2012 |
| WO | 2012046781 A1 | 4/2012 |

OTHER PUBLICATIONS

International Search Report dated Oct. 28, 2014 filed in PCT/JP2014/069695.
Extended European Search Report dated Feb. 28, 2017 issued in the corresponding European patent application No. 14832171.4.

* cited by examiner

METHOD FOR PRODUCING TRANS-BIS(AMINOMETHYL)CYCLOHEXANE, METHOD FOR PRODUCING BIS(ISOCYANATOMETHYL)CYCLOHEXANE, BIS(ISOCYANATOMETHYL)CYCLOHEXANE, POLYISOCYANATE COMPOSITION, AND POLYURETHANE RESIN

TECHNICAL FIELD

The present invention relates to a method for producing trans-bis(aminomethyl)cyclohexane, a method for producing bis(isocyanatomethyl)cyclohexane, bis(isocyanatomethyl)cyclohexane, a polyisocyanate composition, and a polyurethane resin.

BACKGROUND ART

Conventionally, bis(aminomethyl)cyclohexanes are well known for a polyamide material used for fibers and films.

Furthermore, bis(isocyanatomethyl)cyclohexane derived from bis(aminomethyl)cyclohexane is useful for a polyurethane material used for, for example, paints, adhesives, and plastic lenses, and a polyisocyanate composition material used for, for example, a curing agent for paints.

The bis(aminomethyl)cyclohexane includes two stereoisomers of trans-bis(aminomethyl)cyclohexane (hereinafter may be referred to as trans isomer) and cis-bis(aminomethyl)cyclohexane (hereinafter may be referred to as cis isomer), and it has been known that the ratios of the cis isomer and the trans isomer in bis(aminomethyl)cyclohexane affect various physical properties of polyamides and polyurethanes produced by using the bis(aminomethyl)cyclohexane.

For example, in polyamides, a higher trans isomer ratio in bis(aminomethyl)cyclohexane, i.e., the material for polyamides, improves physical properties such as a melting point and thermal stability, and a polyamide that is suitable for fibers and films can be produced.

In polyurethanes, using bis(isocyanatomethyl)cyclohexane derived from bis(aminomethyl)cyclohexane having a high trans isomer ratio as the material for polyurethane allows for production of polyurethane having excellent heat resistance and solubility to solvents.

Therefore, a production method for bis(aminomethyl) cyclohexane having a high trans isomer ratio is desired in various industrial fields.

As a method for producing bis(aminomethyl)cyclohexane having a high trans isomer ratio, the following method for producing trans-1,4-bis(aminomethyl)cyclohexane is proposed: for example, hydrogenated terephthalic acid or its derivative is allowed to contact with ammonia, trans-1,4-dicyanocyclohexane is taken out from the produced 1,4-dicyanocyclohexane by crystallization using an aqueous solvent, and thereafter, the produced trans-1,4-dicyanocyclohexane is allowed to contact with hydrogen. Furthermore, Patent Document 1 has proposed the following: after taking out trans-1,4-dicyanocyclohexane by crystallization, the remaining cis-1,4-dicyanocyclohexane is allowed to contact with ammonia again with hydrogenated terephthalic acid or its derivative for isomerization.

Meanwhile, because crystallization is generally troublesome, when producing trans-bis(aminomethyl)cyclohexane industrially, as described in Patent Document 1, taking out trans-1,4-dicyanocyclohexane by crystallization may cause the process to be complicated. Thus, for simplifying the process, for example, it has also been examined to take out trans-1,4-dicyanocyclohexane from 1,4-dicyanocyclohexane (mixture of cis isomer and trans isomer) by distillation.

CITATION LIST

Patent Document

Patent Document 1: Japanese Unexamined Patent Publication No. 2011-6382

SUMMARY OF THE INVENTION

Problem to be Solved by the Invention

However, in various industrial fields, a method for producing trans-bis(aminomethyl)cyclohexane in more efficient way is desired.

Thus, an object of the present invention is to provide a method for producing trans-bis(aminomethyl)cyclohexane which produces trans-bis(aminomethyl)cyclohexane industrially and more efficiently, a method for producing bis (isocyanatomethyl)cyclohexane in which trans-bis(aminomethyl)cyclohexane produced by the method for producing trans-bis(aminomethyl)cyclohexane is used, bis(isocyanatomethyl)cyclohexane produced by the method for producing bis(isocyanatomethyl)cyclohexane, a polyisocyanate composition produced by using the produced bis(isocyanatomethyl)cyclohexane, and a polyurethane resin produced by using the bis(isocyanatomethyl)cyclohexane or the polyisocyanate composition.

Means for Solving the Problem

A method for producing trans-bis(aminomethyl)cyclohexane of the present invention includes a trans-isomerization step in which cis-dicyanocyclohexane is isomerized into trans-dicyanocyclohexane by heating dicyanocyclohexane containing cis-dicyanocyclohexane in the presence of a tar component produced by distillation of dicyanocyclohexane; and an aminomethylation step in which trans-dicyanocyclohexane produced by the trans-isomerization step is allowed to contact with hydrogen to produce trans-bis(aminomethyl) cyclohexane.

In the method for producing trans-bis(aminomethyl)cyclohexane of the present invention, it is preferable that 2 to 30 parts by mass of the tar component is present relative to 100 parts by mass of the dicyanocyclohexane.

In the method for producing trans-bis(aminomethyl)cyclohexane of the present invention, it is preferable that in the trans-isomerization step, dicyanocyclohexane is distilled using a distillation column and trans-dicyanocyclohexane is taken out from a column top of the distillation column, and the tar component is taken out from a column bottom of the distillation column, and the tar component that is taken out is added to the dicyanocyclohexane.

In the method for producing trans-bis(aminomethyl)cyclohexane of the present invention, it is preferable that the distillation column has a column top temperature of 140° C. or more and 220° C. or less and a column bottom temperature of 200° C. or more and 320° C. or less, and the residence time at the column bottom is 1 hour or more and 50 hours or less.

In a method for producing bis(isocyanatomethyl)cyclohexane of the present invention, the trans-bis(aminomethyl)

cyclohexane produced by the above-described method for producing trans-bis(aminomethyl)cyclohexane is isocyanized.

Bis(isocyanatomethyl)cyclohexane of the present invention is produced by the above-described method for producing bis(isocyanatomethyl)cyclohexane.

A polyisocyanate composition of the present invention is produced by modifying the above-described bis(isocyanatomethyl)cyclohexane, and contains at least one functional group of (a) to (e) below:
(a) an isocyanurate group,
(b) an allophanate group,
(c) a biuret group,
(d) a urethane group, and
(e) a urea group.

A polyurethane resin of the present invention is produced by allowing the above-described bis(isocyanatomethyl)cyclohexane to react with an active hydrogen compound.

A polyurethane resin of the present invention is produced by allowing the above-described polyisocyanate composition to react with an active hydrogen compound.

Effect of the Invention

In the method for producing trans-bis(aminomethyl)cyclohexane of the present invention, dicyanocyclohexane containing cis-dicyanocyclohexane is heated in the presence of a tar component produced by distillation of dicyanocyclohexane to isomerize cis-dicyanocyclohexane into trans-dicyanocyclohexane. Therefore, trans-dicyanocyclohexane can be produced more efficiently, and trans-bis(aminomethyl)cyclohexane can be produced with excellent efficiency.

In the method for producing bis(isocyanatomethyl)cyclohexane of the present invention, trans-bis(aminomethyl)cyclohexane produced by the above-described method for producing trans-bis(aminomethyl)cyclohexane is used, and therefore bis(isocyanatomethyl)cyclohexane can be produced more efficiently.

Bis(isocyanatomethyl)cyclohexane of the present invention is produced by the above-described method for producing bis(isocyanatomethyl)cyclohexane, and therefore can be produced more efficiently.

In the polyisocyanate composition of the present invention, the above-described bis(isocyanatomethyl)cyclohexane is used, and therefore the polyisocyanate composition of the present invention can be produced more efficiently.

The polyurethane resin of the present invention is produced by using the bis(isocyanatomethyl)cyclohexane of the present invention, or the polyisocyanate composition of the present invention, and therefore can be produced more efficiently.

DESCRIPTION OF EMBODIMENTS

In the method for producing trans-bis(aminomethyl)cyclohexane of the present invention, although to be described later in detail, dicyanocyclohexane containing cis-dicyanocyclohexane is distilled, and after cis-dicyanocyclohexane is isomerized into trans-dicyanocyclohexane, the produced trans-dicyanocyclohexane is allowed to contact with hydrogen to produce trans-bis(aminomethyl)cyclohexane.

Examples of dicyanocyclohexane include 1,2-dicyanocyclohexane, 1,3-dicyanocyclohexane, 1,4-dicyanocyclohexane, and a mixture of them. These examples of dicyanocyclohexane may be used singly or in combination of two or more. For the dicyanocyclohexane, preferably 1,3-dicyanocyclohexane and 1,4-dicyanocyclohexane are used, and more preferably 1,4-dicyanocyclohexane is used.

The dicyanocyclohexane is not particularly limited as long as cis-dicyanocyclohexane is contained, and generally, a stereoisomer mixture of cis isomer (cis-dicyanocyclohexane) and trans isomer (trans-dicyanocyclohexane) is used.

Such dicyanocyclohexane can be obtained, for example, as a commercially available product, or can be produced by a known method from, for example, phthalic acids, phthalic acid esters, and phthalic acid amides.

In the following, a method for producing dicyanocyclohexane, and producing trans-bis(aminomethyl)cyclohexane from the produced dicyanocyclohexane is described with reference to the plant shown in FIG. 1.

Figure 1:
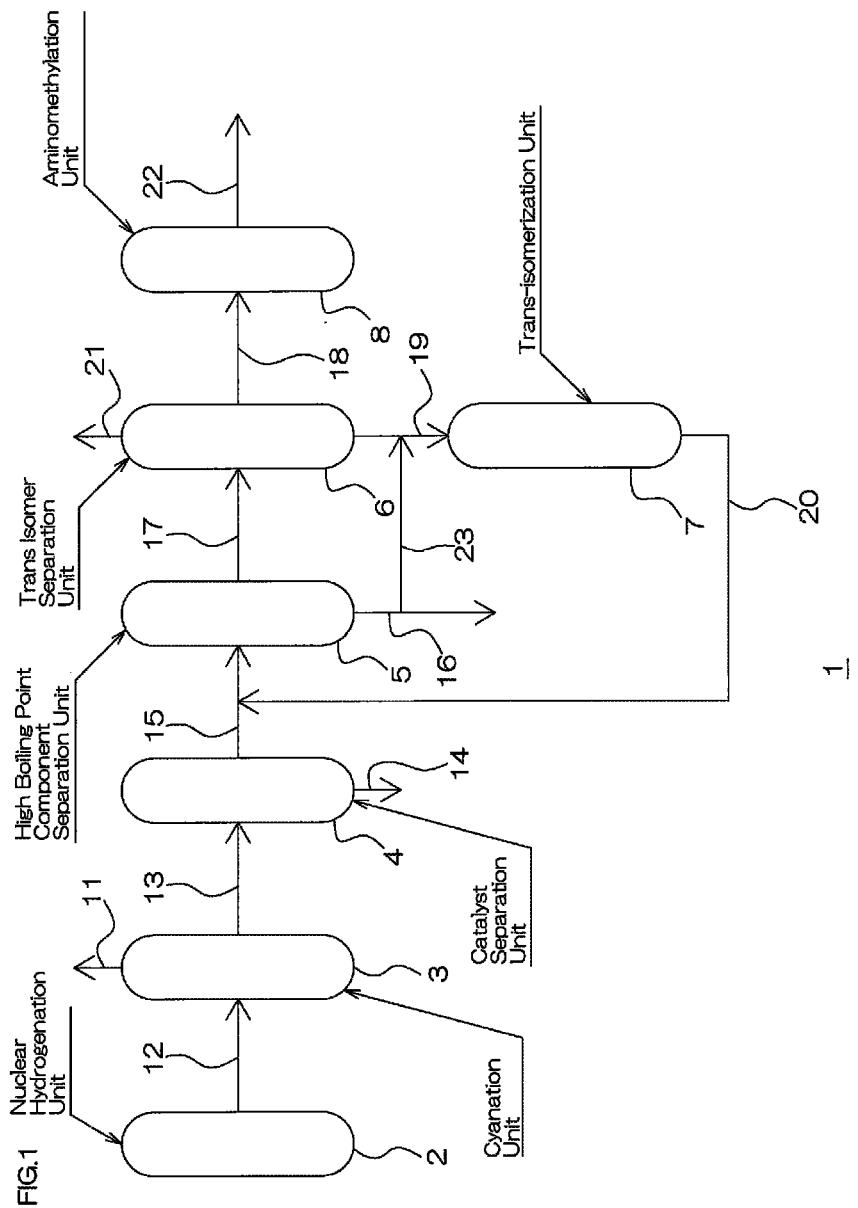
FIG. 1 is a schematic diagram illustrating an embodiment of a plant in which the method for producing trans-bis(aminomethyl)cyclohexane of the present invention is used.

In FIG. 1, a plant 1 is a production system for producing trans-bis(aminomethyl)cyclohexane, and includes a nuclear hydrogenation unit 2, a cyanation unit 3, a catalyst separation unit 4, a high boiling point component separation unit 5, a trans isomer separation unit 6, a trans isomerization unit 7, and an aminomethylation unit 8.

The nuclear hydrogenation unit 2 is composed of, for example, a known reaction tank, and is provided as a unit for allowing phthalic acids of at least one selected from the group consisting of phthalic acids, phthalic acid esters, and phthalic acid amides or a derivative thereof to contact with hydrogen to perform nuclear hydrogenation reaction.

To be specific, in the nuclear hydrogenation unit 2, phthalic acids of at least one selected from the group consisting of phthalic acids, phthalic acid esters, and phthalic acid amides or a derivative thereof is subjected to nuclear hydrogenation, thereby producing corresponding hydrogenated phthalic acids or a derivative thereof (that is, hydrogenated phthalic acids of at least one selected from the group consisting of cyclohexanedicarboxylic acids, cyclohexanedicarboxylic acid esters, and cyclohexanedicarboxylic acid amides or a derivative thereof) (nuclear hydrogenation step).

Examples of phthalic acids include phthalic acid (ortho-phthalic acid), isophthalic acid (meta-phthalic acid), and terephthalic acid (para-phthalic acid).

These phthalic acids or a derivative thereof may be used singly or in combination of two or more.

The substituted positions of the functional groups of the hydrogenated phthalic acids or a derivative thereof obtained in the nuclear hydrogenation step correlate with the ortho-, meta-, or para-form of phthalic acids or a derivative thereof as the material component.

That is, for example, when isophthalic acid or a derivative thereof is used as the phthalic acids or a derivative thereof, the produced hydrogenated phthalic acids or a derivative thereof is hydrogenated phthalic acids of at least one selected from the group consisting of cyclohexane-1,3-dicarboxylic acid, cyclohexane-1,3-dicarboxylic acid ester, cyclohexane-1,3-dicarboxylic acid amide or a derivative thereof; when terephthalic acid or a derivative thereof is used, the produced hydrogenated phthalic acids or a derivative thereof is hydrogenated phthalic acids or a derivative thereof of at least one selected from the group consisting of cyclohexane-1,4-dicarboxylic acid, cyclohexane-1,4-dicarboxylic acid ester, and cyclohexane-1,4-dicarboxylic acid amide.

In the nuclear hydrogenation step, for example, the method described in Japanese Unexamined Patent Publication No. 2001-181223 may be used.

The phthalic acids or a derivative thereof used as a material in the present invention may be one having quality of industrially available products, and also undried (containing water) phthalic acids or a derivative thereof that have undergone the hydrogenation purifying step generally performed in production of phthalic acids may be used.

The reaction in the nuclear hydrogenation step is exothermic reaction, and therefore to suitably suppress the temperature increase due to the heat of reaction, and also to increase conversion, it is preferable that a solvent that is inactive in such a reaction is added as a diluent to the material phthalic acids or a derivative thereof for dilution so that the phthalic acids or a derivative thereof concentration in the reaction solution is, for example, 1 to 50 mass %, preferably 2 to 30 mass %. When the concentration in the reaction solution is within the range, it is advantageous in that the reaction rate is not reduced, and the temperature increase in the reactor is small.

Examples of such a solvent include aqueous solvents such as water, methanol, ethanol, 1-propanol, isopropanol, 1-butanol, 2-butanol, sec-butanol, t-butanol, and 1,4-dioxane.

Use of such an aqueous solvent is advantageous in that the reaction mixture in the nuclear hydrogenation step can be cooled as necessary, and re-circulated for use.

In this case, water is used preferably because it can be recovered by separation operation thereafter; it does not allow unwanted components to be mixed into the reaction system; and undried phthalic acids that underwent the purification step of phthalic acids can be used.

In the nuclear hydrogenation step, hydrogen used in the nuclear hydrogenation may be of industrial use quality. For example, the hydrogen may contain inactive gas (e.g., nitrogen, methane, etc.) but its hydrogen concentration is preferably 50% or more.

The hydrogen amount is preferably about 3 to 50 times the material phthalic acids or a derivative thereof in molar ratio.

When the hydrogen amount is within such a range, the amount of unreacted materials is small, the reaction rate is sufficient, and it is advantageous economically.

In the nuclear hydrogenation step, a known catalyst may be added.

The catalyst used in the nuclear hydrogenation step is a general noble metal catalyst for nuclear hydrogenation. To be specific, examples of such a catalyst include palladium, platinum, ruthenium, and rhodium, and preferably, palladium or ruthenium is used.

These catalysts are preferably prepared as a supported catalyst. Examples of supports for such catalysts include activated carbon, alumina, silica, and kieselguhr, and preferably, activated carbon or silica is used.

The amount of metal (e.g., palladium, platinum, ruthenium, rhodium, etc.) supported is, for example, 0.1 to 10 mass %, preferably 0.5 to 10 mass % of the total amount including the catalyst support.

When the amount of metal supported is within such a range, it is preferable because the activity of catalyst per weight is high.

The catalyst is used in the form of, for example, powder, granular, or may be supported on a pellet support. Preferably, the catalyst is in the form of powder. When the catalyst has a suitable size, for example, when the catalyst is powder, the internal portion in the catalyst that effectively contributes to reaction is large, and reaction rate does not easily decrease.

The amount of the catalyst relative to 100 parts by mass of the phthalic acids or a derivative thereof is, for example, 0.1 to 50 parts by mass, preferably 0.5 to 20 parts by mass.

The phthalic acids or a derivative thereof is not highly soluble in general solvents such as water, and therefore the reaction is preferably performed by liquid-phase suspension reaction.

The reactor is preferably a pressure-resistant vessel.

A material slurry and hydrogen are introduced from the reactor top or bottom, and brought into contact with the catalyst in a suspension. After the reaction, the product, i.e., hydrogenated phthalic acids or a derivative thereof, is highly soluble in a general solvent such as water at high temperature, and therefore separation from the catalyst can be performed by filtration.

In the filtration, the above-described product is dissolved in, for example, a known alkaline solution (e.g., aqueous sodium hydroxide solution, etc.), and after the solution is filtered, the solution can be neutralized by a known acid solution (e.g., aqueous hydrogen chloride solution, etc.).

Thereafter, by drying or concentrating the product, or by crystallizing the product by temperature reduction, hydrogenated phthalic acids or a derivative thereof can be obtained.

The reaction temperature is usually in the range of 50 to 200° C., and preferably 100 to 160° C.

The reaction temperature within such a range is advantageous in that the amount of unreacted materials and by-products is less, hydrogenolysis does not occur easily, and as a result, the yield increases.

The reaction pressure is usually in the range of 0.5 to 15 MPa, preferably 2 to 15 MPa, more preferably 2 to 8 MPa, even more preferably 2 to 5 MPa.

The reaction pressure within such a range is advantageous in that the reaction rate does not easily decrease, and the amount of by-products is less.

The conversion rate of phthalic acids or a derivative thereof is usually 90% or more, preferably 95% or more, and more preferably 98% or more.

When the amount of the unreacted phthalic acids or a derivative thereof is small as described above, it is advantageous in that burdens in post-treatment are reduced.

The hydrogenated phthalic acids or a derivative thereof obtained in the nuclear hydrogenation step have a functional group at substitution positions correlating with the ortho-, meta-, or para-form of the phthalic acids or a derivative thereof used as the material, and is a mixture of cis isomer and trans isomer.

To be more specific, for example, when isophthalic acid or an isophthalic acid derivative (meta-phthalic acid) is used as the material, the hydrogenated phthalic acids or a derivative thereof to be produced is a mixture of 1,3 position-cis isomer (that is, cis-cyclohexane-1,3-dicarboxylic acid, cis-cyclohexane-1,3-dicarboxylic acid ester, and/or cis-cyclohexane-1,3-dicarboxylic acid amide), and 1,3-position trans isomer (that is, trans-cyclohexane-1,3-dicarboxylic acid, trans-cyclohexane-1,3-dicarboxylic acid ester, and/or trans-cyclohexane-1,3-dicarboxylic acid amide); and when terephthalic acid or a terephthalic acid derivative (para-phthalic acid) is used as the material, the hydrogenated phthalic acids or a derivative thereof to be produced is a mixture of 1,4 position-cis isomer (that is, cis-cyclohexane- 1,4-dicarboxylic acid, cis-cyclohexane-1,4-dicarboxylic acid ester, and/or cis-cyclohexane-1,4-dicarboxylic acid amide), and 1,4 position-trans isomer (that is, trans-cyclohexane-1,4-dicarboxylic acid, trans-cyclohexane-1,4-dicarboxylic acid ester, and/or trans-cyclohexane-1,4-dicarboxylic acid amide).

Furthermore, for example, when isophthalic acid or an isophthalic acid derivative (meta-phthalic acid), and terephthalic acid or a terephthalic acid derivative (para-phthalic acid) are used in combination as the materials, the hydrogenated phthalic acids or a derivative thereof to be produced are a mixture of the above-described 1,3-position cis isomer, 1,3-position trans isomer, 1,4-position cis isomer, and 1,4-position trans isomer.

The produced hydrogenated phthalic acids or a derivative thereof is taken out from the nuclear hydrogenation unit 2 through the transport line 12, and is fed to the cyanation unit 3.

The cyanation unit 3 is composed of, for example, a known reaction tank, and is provided as a unit for allowing the hydrogenated phthalic acids or a derivative thereof to contact with ammonia to perform cyanation reaction.

To be specific, in the cyanation unit 3, the hydrogenated phthalic acids or a derivative thereof produced in the above-described nuclear hydrogenation step is allowed to contact with ammonia to produce dicyanocyclohexane (cyanation step).

In the cyanation step, for example, the method described in Japanese Unexamined Patent Publication No.S 63-10752 may be used.

To be more specific, in the cyanation step, the hydrogenated phthalic acids or a derivative thereof obtained in the nuclear hydrogenation step is allowed to react with a compound capable of serving as an ammonia supply source (e.g., ammonia, urea, ammonium carbonate, etc.)(hereinafter may be referred to as ammonia supply source compound) by heating at, usually 200° C. or more and below 350° C., preferably 230° C. or more and below 320° C.

The reaction temperature within such a range is advantageous in that the reaction rate does not decrease, and decomposition due to excessive heating occurs less.

In the cyanation step, metal oxide may be used as a catalyst.

Examples of the metal oxide include silica, alumina, phosphorus pentoxide, tin oxide, titanium oxide, zinc oxide, iron oxide, zirconium oxide, and cobalt oxide.

Of these metal oxides, in view of easy separation after reaction, silica, alumina, tin oxide, titanium oxide, zinc oxide, iron oxide, zirconium oxide, or cobalt oxide is preferably used.

In this step, furthermore, metal oxide and other catalysts can be used in combination, and examples of such a catalyst include mineral acids such as hydrochloric acid, phosphoric acid, and sulfuric acid, and organic acids such as acetic acid, propionic acid, and benzoic acid.

When metal oxide and other catalyst are used in combination, the mixing ratio of these is not particularly limited, and is set suitably in accordance with the purpose and application.

The catalyst is used in the form of, for example, powder, granular, or may be supported on a pellet support. Preferably, the catalyst is in the form of powder.

When the catalyst has a suitable size, for example, when the catalyst is powder, the internal portion in the catalyst that effectively contributes to reaction is large, and reaction rate does not easily decrease.

The amount of catalyst relative to 100 parts by mass of hydrogenated phthalic acids or a derivative thereof is, for example, 0.1 to 50 parts by mass, preferably 0.5 to 20 parts by mass.

In the reaction, a solvent is preferably used as appropriate.

Examples of the solvent include, although any solvent that does not inhibit the purpose of the method of the present invention can be used, aliphatic or alicyclic hydrocarbons such as decane, undecane, dodecane, tridecane, tetradecane, pentadecane, and decalin; aromatic hydrocarbons such as mesitylene, tetralin, butylbenzene, p-cymene, diethylbenzene, diisopropylbenzene, triethylbenzene, cyclohexylbenzene, dipentylbenzene, and dodecylbenzene; alcohols such as hexanol, 2-ethylhexanol, octanol, decanol, dodecanol, ethylene glycol, diethylene glycol, and triethylene glycol; ethers such as diethylene glycol dimethylether, triethylene glycol dimethylether, tetraethylene glycol dimethylether, o-dimethoxybenzene, ethylphenylether, butylphenylether, and o-diethoxybenzene: halogenated aromatic hydrocarbons such as iodobenzene, o-dichlorobenzene, m-dichlorobenzene, 1,2,4-trichlorobenzene, o-dibromobenzene, bromochlorobenzene, o-chlorotoluene, p-chlorotoluene, p-chloroethylbenzene, and 1-chloronaphthalene; polar aprotic solvents such as dimethyl sulfoxide, N,N-dimethylformamide, N,N-dimethylacetamide, hexamethylphosphoramide, N,N'-dimethylimidazolidinone, N,N'-diethylimidazolidinone, N,N'-dipropylimidazolidinone, N,N',4-trimethylimidazolidinone, N,N'-dimethylpropyleneurea, N-methyl-2-pyrrolidone, and N-ethyl-2-pyrrolidone; and the product in this step, i.e., 1,4-dicyanocyclohexane. These solvents may be used singly or in combination of two or more.

As the solvent, in view of suppressing deposition of dicyanocyclohexanes to the gas discharge pipe of the reactor, and to apparatuses at downstream of the reactor such as a dehydration apparatus, the solvent is preferably selected from, for example, ethers such as diethylene glycol dimethylether, triethylene glycol dimethylether, tetraethylene glycol dimethylether, o-dimethoxybenzene, ethylphenylether, butylphenylether, and o-diethoxybenzene; halogenated aromatic hydrocarbons such as iodobenzene, o-dichlorobenzene, m-dichlorobenzene, 1,2,4-trichlorobenzene, o-dibromobenzene, bromochlorobenzene, o-chlorotoluene, p-chlorotoluene, p-chloroethylbenzene, and 1-chloronaphthalene; polar aprotic solvents such as dimethyl sulfoxide, N,N-dimethylformamide, N,N-dimethylacetamide, hexamethylphosphoramide, N,N'-dimethylimidazolidinone, N,N'-diethylimidazolidinone, N,N'-dipropylimidazolidinone, N,N',4-trimethylimidazolidinone, N,N'-dimethylpropyleneurea, N-methyl-2-pyrrolidone, and N-ethyl-2-pyrrolidone.

Of the above-described solvents, those solvents having a boiling point of 180° C. to 350° C. is preferably used. Use of the solvent having a boiling point lower than 180° C. is not preferable because the energy load on the reactor increases. Use of the solvent having a boiling point higher than 350° C. is not preferable because the effects of suppressing the deposition of dicyanocyclohexane to the reactor gas discharge pipe and to apparatuses at downstream of the reactor such as a dehydration apparatus decreases.

In view of the above, of the above-described solvents, selection is made preferably from o-dichlorobenzene, triethylene glycol dimethylether, tetraethylene glycol dimethylether, and polar aprotic solvents such as N,N'-dimethylimidazolidinone, N,N'-diethylimidazolidinone, N,N'-dipropylimidazolidinone, N,N',4-trimethylimidazolidinone, N,N'-dimethylpropyleneurea, N-methyl-2-pyrrolidone, and N-ethyl-2-pyrrolidone.

The amount of solvent used is not particularly limited, and usually is 10 times or less by weight the reactant (including the above-described hydrogenated phthalic acids or a derivative thereof obtained in the nuclear hydrogenation step), preferably 1 time or less by weight the reactant, and more preferably 3 to 50 parts by mass relative to 100 parts by mass of the hydrogenated phthalic acid or a derivative thereof. When the amount of the solvent is small, or when no solvent is used, suppression of deposition of dicyanocyclohexane to the gas discharge pipe of the reactor and to apparatuses at downstream of the reactor such as a dehydration apparatus becomes difficult, and when the amount of the solvent is large, it is not preferable because energy burden on the reactor increases.

The reaction method is not particularly limited, and examples thereof include slurry-bed batch process, semi-batch process, and continuous process; and also fixed-bed continuous process. Preferably, liquid-phase slurry reaction is used.

The reactor is preferably a pressure-resistant vessel.

For example, hydrogenated phthalic acids or a derivative thereof, and a catalyst are introduced from the reactor top or bottom, and the hydrogenated phthalic acids or a derivative thereof are dissolved by heating to be suspended; and an ammonia supply source compound such as ammonia is fed intermittently or continuously to the reactor, to allow reaction at a predetermined temperature.

The amount of the ammonia supply source compound to be fed is, in view of facilitating treatment or recovery of ammonia after reaction, for example, 1 to 20 mol, preferably 2 to 20 mol relative to 1 mol of hydrogenated phthalic acids or a derivative thereof.

The feeding rate of the ammonia supply source compound is not particularly limited, and preferably 0.1 mol to 2 mol per 1 hour relative to 1 mol of hydrogenated phthalic acids or a derivative thereof, and more preferably, more than 0.5 mol and 2 mol or less (that is, more than 0.5 mol equivalent/hydrogenated terephthalic acid or terephthalic acid derivative/hr and 2 mol equivalent/hydrogenated terephthalic acid or terephthalic acid derivative/hr or less). The feeding rate lower than 0.5 mol relative to 1 mol of hydrogenated phthalic acids or a derivative thereof per 1 hour is not preferable because the reaction requires a long time. The feeding rate higher than 2 mol relative to 1 mol of hydrogenated phthalic acids or a derivative thereof per 1 hour is disadvantageous economically in that a large amount of the unreacted ammonia supply source compound is present, and therefore, for example, when ammonia is to be recovered and reused, the burden is substantial.

The feeding time is suitably selected depending on the feeding rate. For example, the feeding time is 1 to 80 hours, preferably 2 to 50 hours.

Water is produced as a by-product in this reaction, and therefore in view of accelerating the reaction, water is preferably removed out of the system. To remove water out of the system, for example, an inactive gas such as nitrogen can be fed to the reactor.

The reaction may be performed under any pressure condition, for example, under elevated pressure, ambient pressure, and reduced pressure, which is suitably selected.

After the reaction, the product dicyanocyclohexane are obtained as a mixture (mixture of stereoisomers) of the cis isomer and trans isomer.

The dicyanocyclohexane obtained in the cyanation step have a functional group at substitution positions correlating with the ortho-, meta-, or para-form of the phthalic acids or a derivative thereof used as the material, and is a mixture of cis isomer and trans isomer.

To be more specific, for example, when isophthalic acid or an isophthalic acid derivative is used as the material, dicyanocyclohexane to be produced is a mixture of 1,3 position-cis isomer (that is, cis-1,3-dicyanocyclohexane) and 1,3-position trans isomer (that is, trans-1,3-dicyanocyclohexane); and for example, when terephthalic acid or a terephthalic acid derivative (para-phthalic acid) is used as the material, dicyanocyclohexane to be produced is a mixture of 1,4 position-cis isomer (that is, cis-1,4-dicyanocyclohexane) and 1,4 position-trans isomer (that is, trans-1,4-dicyanocyclohexane).

Furthermore, for example, 3 when isophthalic acid or an isophthalic acid derivative (meta-phthalic acid) and terephthalic acid or a terephthalic acid derivative (para-phthalic acid) are used in combination as the materials, the dicyanocyclohexane to be produced is a stereoisomer mixture of the above-described 1,3-position cis isomer, 1,3-position trans isomer, 1,4-position cis isomer, and 1,4-position trans isomer.

The dicyanocyclohexane obtained after the reaction converges to the equilibrium composition ratio of dicyanocyclohexane at the reaction temperature, approximately, to cis isomer/trans isomer=40/60 to 60/40, regardless of the stereo isomer ratio of the hydrogenated phthalic acids or a derivative thereof.

The unreacted ammonia supply source compound is taken out from the cyanation unit 3 through the recovery line 11, and recovered and reused.

In the above-described cyanation step, dicyanocyclohexane is obtained as a mixture containing, for example, a catalyst such as metal oxide, and furthermore a reaction intermediate in the cyanation reaction, and a high boiling point component such as by-products.

Thus, in the plant 1, the catalyst and the high boiling point component are separated and recovered.

To be specific, in the plant 1, the mixture (mixture containing dicyanocyclohexane, catalyst, and high boiling point component) produced in the above-described cyanation step is taken out from the cyanation unit 3 through the transport line 13, and then fed to the catalyst separation unit 4.

The catalyst separation unit 4 is provided as a unit for separating the catalyst from the mixture. In the catalyst separation unit 4, the catalyst is separated from the above-described mixture (catalyst separation step).

The catalyst can be separated by any method without particular limitation, and known separation methods such as distillation, filtering, and extraction can be used. The separated catalyst is recovered through a catalyst recovery line 14 connected to the catalyst separation unit 4, and as necessary reused.

Meanwhile, the mixture (mixture containing dicyanocyclohexane and high boiling point component) from which the catalyst is removed is taken out from the catalyst separation unit 4 through the transport line 15, and fed to the high boiling point component separation unit 5.

The high boiling point component separation unit 5 is composed of, for example, a known distillation column, and is provided as a unit for separating the high boiling point component from the above-described mixture. By distilling the above-described mixture in the high boiling point component separation unit 5, the high boiling point component is separated (high boiling point component separation step).

The distillation conditions in the high boiling point component separation unit 5 are as follows: to be specific, the distillation column has a column top pressure of, for example, 2 kPa or more, preferably 3 kPa or more, and for example, 10 kPa or less, preferably 5 kPa or less.

The distillation column has a column top temperature of, for example, 130° C. or more, preferably 140° C. or more, and for example, 200° C. or less, preferably 190° C. or less. The distillation column has a column bottom temperature of, for example, 160° C. or more, preferably 180° C. or more, and for example, 280° C. or less, preferably 260° C. or less.

The residence time at the column bottom is, for example, 0.01 hour or more, preferably 0.1 hour or more, and for example, 50 hours or less, preferably 25 hours or less.

In this manner, the high boiling point component is separated as a column bottom component from the above-described mixture, and recovered through the discharge line 16.

Meanwhile, the mixture (stereoisomers mixture of dicyanocyclohexane) from which the high boiling point component is separated (removed) is taken out from the high boiling point component separation unit 5 through the transport line 17, and fed to the trans isomer separation unit 6.

The trans isomer separation unit 6 is composed of, for example, a known distillation column, and is provided as a unit for separating (purifying) trans-dicyanocyclohexane from the mixture of stereoisomers of dicyanocyclohexane.

In the trans isomer separation unit 6, mixture of stereoisomers of the above-described dicyanocyclohexane is distilled to separate (purify) the trans-dicyanocyclohexane (trans isomer separation step).

The specific distillation conditions of the trans isomer separation unit 6 are as follows: the distillation column has a column top pressure of, for example, 3 kPa or more, preferably 4 kPa or more, and for example, 30 kPa or less, preferably 15 kPa or less.

The distillation column has a column top temperature of, for example, 130° C. or more, preferably 140° C. or more, and for example, 200° C. or less, preferably 190° C. or less. The distillation column has a column bottom temperature of, for example, 160° C. or more, preferably 180° C. or more, and for example, 280° C. or less, preferably 260° C. or less.

The residence time at the column bottom is for example, 0.1 hours or more, preferably 0.2 hours or more, and for example, 50 hours or less, preferably 25 hours or less.

The distillation conditions within the above-described range allow for separation (purification) of trans-dicyanocyclohexane in the stereoisomers mixture.

Generally, cis-dicyanocyclohexane is isomerized into trans by heat to produce trans-dicyanocyclohexane. Therefore, for example, when trans-dicyanocyclohexane is distilled from the mixture of stereoisomers, the heating at the time of distillation may also cause cis-dicyanocyclohexane in the mixture of stereoisomers to be isomerized into trans.

The purity of the produced trans-dicyanocyclohexane (trans isomer ratio) can be suitably controlled in accordance with the conditions of reaction and separation, and is about 80% or more, preferably 82% or more, more preferably 85% or more.

In the distillation, the organic solvent used in the cyanation step can be recovered as a column top component through the solvent recovery line 21. The recovered organic solvent can be reused as necessary.

Meanwhile, cis-dicyanocyclohexane remained in the above-described distillation is taken out from the trans isomer separation unit 6 through the transport line 19, and transported into the trans isomerization unit 7.

The trans isomerization unit 7 is composed of, for example, a known reaction tank, and is provided as a unit for isomerizing cis-dicyanocyclohexane into trans-dicyanocyclohexane.

In the plant 1, the above-described cis-dicyanocyclohexane is heated in the trans isomerization unit 7 to be isomerized into trans to produce trans-dicyanocyclohexane (trans-isomerization step).

The specific heating conditions in the trans isomerization unit 7 are as follows: the heating temperature of, for example, 200° C. or more, preferably 220° C. or more, and for example, 320° C. or less, preferably 300° C. or less.

The heating time is, for example, 1 hour or more, preferably 2 hours or more, and for example, 50 hours or less, preferably 25 hours or less.

The heating conditions within the above-described range allow for excellent isomerization of cis-dicyanocyclohexane into trans.

Generally, in the trans isomerization unit 7, a mixture of stereoisomers of cis-dicyanocyclohexane and trans-dicyanocyclohexane is produced. The molar ratio of cis isomer (cis-dicyanocyclohexane) to trans isomer (trans-dicyanocyclohexane) converges the equilibrium composition ratio of dicyanocyclohexane, approximately, to cis isomer/trans isomer=40/60 to 60/40.

The dicyanocyclohexane (mixture of stereoisomers) produced in the trans isomerization unit 7 is taken out from the trans isomerization unit 7 through the returning line 20, and is returned to the transport line 15. Then, along with the dicyanocyclohexane (mixture of stereoisomers) taken out from the catalyst separation unit 4, fed to the high boiling point component separation unit 5 again.

In this manner, dicyanocyclohexane can be effectively used, and the yield can be improved.

In the above-described trans-isomerization step, cis-dicyanocyclohexane is isomerized into trans-dicyanocyclohexane in the presence of a tar component produced by distillation of dicyanocyclohexane.

To be specific, for example, a portion of the high boiling point component (tar component) recovered by distillation in the high boiling point component separation unit 5 is taken out (ref: FIG. 1), for example, from an ejection line 23 branched from a discharge line 16, and fed to dicyanocyclohexane in the transport line 19.

Then, in the trans isomerization unit 7, in the presence of the above-described tar component, cis-dicyanocyclohexane is distilled to be isomerized into trans.

By isomerizing cis-dicyanocyclohexane into trans in the presence of a tar component as described above, efficiency of isomerization into trans can be improved.

The mixing ratio of the tar component relative to dicyanocyclohexane is as follows: relative to 100 parts by mass of a total amount of dicyanocyclohexane, for example, 2 parts by mass or more, preferably 5 parts by mass or more, for example, 30 parts by mass or less, preferably 20 parts by mass or less of the tar component in the trans isomerization unit 7.

When the ratio of the tar component is within the above-described range, cis-dicyanocyclohexane can be isomerized into trans with excellent efficiency.

Meanwhile, trans-dicyanocyclohexane separated in the trans isomer separation unit 6 is transported to the aminomethylation unit 8 through the transport line 18.

The aminomethylation unit 8 is composed of, for example, a known reaction tank, and is provided as a unit for allowing trans-dicyanocyclohexane to contact with hydrogen to subject trans-dicyanocyclohexane to aminomethylation.

In the plant 1, in the aminomethylation unit 8, trans-dicyanocyclohexane produced in the above-described trans-isomerization step is allowed to contact with hydrogen to produce trans-bis(aminomethyl)cyclohexane (aminomethylation step).

In the aminomethylation step, for example, the method described in, for example, Japanese Unexamined Patent Publication No. 2001-187765 can be used.

An industrial use hydrogen is sufficient in terms of quality as the hydrogen used in the aminomethylation step, and the hydrogen may contain inactive gas (e.g., nitrogen, methane, etc.). The hydrogen concentration is preferably 50% or more.

As the hydrogenation catalyst used in the aminomethylation step, a known hydrogenation catalyst, for example, any of a cobalt catalyst, a nickel catalyst, a copper catalyst, and a noble metal catalyst can be used.

In view of reactivity and selectivity, a catalyst mainly composed of nickel, cobalt and/or ruthenium is preferably used, and more preferably, Raney catalyst or a catalyst supported on porous metal oxides such as silica, alumina, silica alumina, kieselguhr, and activated carbon is preferably used.

The catalyst may further contain metals such as aluminum, zinc, and silicon.

These hydrogenation catalysts may contain, as a reaction accelerator, a metal selected from chromium, iron, cobalt, manganese, tungsten, and molybdenum.

The hydrogenation catalyst can be used as a perfect solid catalyst, or can be used as a supported solid catalyst, for example, nickel, cobalt, or ruthenium supported on aluminum oxide, titanium oxide, zirconium oxide, magnesia-alumina, etc.

The catalyst is used in the form of, for example, powder, granular, or may be supported on a pellet support. Preferably, the catalyst is in the form of powder. When the catalyst has a suitable size, for example, when the catalyst is powder, the internal portion in the catalyst that effectively contributes to reaction is large, and reaction rate does not easily decrease.

The amount of the catalyst used relative to 100 parts by mass of trans-dicyanocyclohexane is, in view of reactivity and selectivity, for example, 0.1 to 20 parts by mass, preferably 0.5 to 15 parts by mass.

For the reaction, a solvent can be used suitably, and examples of such a solvent include aqueous solvents such as water; alcohols such as methanol, ethanol, 1-propanol, isopropanol, 1-butanol, 2-butanol, and t-butanol; and 1,4-dioxane.

The reaction solution has a trans-dicyanocyclohexane concentration of, for example, 1 to 50 mass %, preferably 2 to 40 mass %.

The trans-dicyanocyclohexane concentration of the reaction solution within such a range is advantageous in that the reaction rate does not decrease, and the temperature increase in the reactor is small.

The reaction is preferably performed in the presence of ammonia.

The ammonia works to suppress production of by-products such as secondary amines, tertiary amines, and polyamines other than the target trans-bis(aminomethyl)cyclohexane, that is, the ammonia improves reaction selectivity.

The amount of ammonia used is, in view of suppressing the above-described by-products, preventing decrease in hydrogenation speed, and making treatment or recovery of ammonia after reaction, for example, 0.05 to 5 mol, preferably 0.1 to 2.5 mol relative to 1 mol of trans-dicyanocyclohexane.

The reaction method is not particularly limited, and examples thereof include slurry-bed batch process, semi-batch process, and continuous process; and also fixed-bed continuous process. Preferably, liquid-phase slurry reaction is used.

The reactor is preferably a pressure-resistant vessel.

For example, trans-dicyanocyclohexane, a catalyst, hydrogen, and as necessary a solvent and ammonia are introduced from the top or the bottom of the reactor, and they are allowed to react at a predetermined temperature.

The reaction pressure is usually 0.1 to 20 MPa, preferably 0.5 to 10 MPa, more preferably 0.5 to 8 MPa, and particularly preferably 0.5 to 5 MPa.

The reaction temperature is, in view of reactivity and selectivity, for example, 50 to 250° C., preferably 50 to 200° C., more preferably 70 to 150° C., and preferably, the reaction temperature is increased during the hydrogenation reaction continuously or stepwise.

After the reaction, trans-bis(aminomethyl)cyclohexane can be separated from the reaction solution by a known method such as filtration and distillation.

The trans-bis(aminomethyl)cyclohexane produced by the aminomethylation step includes functional groups at substitution positions correlating with the ortho-, meta-, or para-form of phthalic acids or a derivative thereof used as the material.

To be more specific, for example, when isophthalic acid or a derivative thereof is used as the material, trans-1,3-bis(aminomethyl)cyclohexane is obtained, and for example, when terephthalic acid or a derivative thereof (para-form) is used as the material, trans-1,4-bis(aminomethyl)cyclohexane is produced.

The purity of trans-bis(aminomethyl)cyclohexane (trans isomer ratio) can be suitably adjusted based on the conditions for reaction and separation, but approximately 80% or more, preferably 85% or more, and more preferably 90% or more.

The obtained trans-bis(aminomethyl)cyclohexane is discharged from the aminomethylation unit through the discharge line 22, purified as necessary, and then thereafter fed to another plant or reserved.

In the method for producing trans-bis(aminomethyl)cyclohexane, by heating dicyanocyclohexane containing cis-dicyanocyclohexane in the presence of a tar component produced by distillation of dicyanocyclohexane, cis-dicyanocyclohexane is isomerized into trans-dicyanocyclohexane. Therefore, trans-dicyanocyclohexane can be produced more efficiently, and trans-bis(aminomethyl)cyclohexane can be produced with more efficiency.

The above-described method includes a nuclear hydrogenation step, a cyanation step, and an aminomethylation step, but for example, the nuclear hydrogenation step can be omitted by using hydrogenated phthalic acids or a derivative thereof as a starting material, and the cyanation step and the aminomethylation step can be performed by using commercial hydrogenated phthalic acids or a derivative thereof (that is, hydrogenated phthalic acids or a derivative thereof of at least one selected from the group consisting of cyclohexanedicarboxylic acids, cyclohexanedicarboxylic acid esters, and cyclohexanedicarboxylic acid amides).

In the above-described method, from the dicyanocyclohexane produced in the cyanation step, first, the high boiling point component is separated in the high boiling point component separation step, and then trans-dicyanocyclohexane is separated in the trans isomer separation step, and thereafter, cis-dicyanocyclohexane is isomerized into trans in the trans-isomerization step. In the above-described method, units are provided individually for each of the steps. However, for example, without providing the units individually for each of the steps, for example, the high boiling point component separation step, the trans isomer separation step, and the trans-isomerization step can be performed at once in one distillation column.

In the following, with reference to FIG. 2, performing the high boiling point component separation step, the trans isomer separation step, and the trans-isomerization step in one distillation column all together is described. The units described above have the same reference numerals in FIG. 2, and detailed descriptions thereof are omitted.

Figure 2:
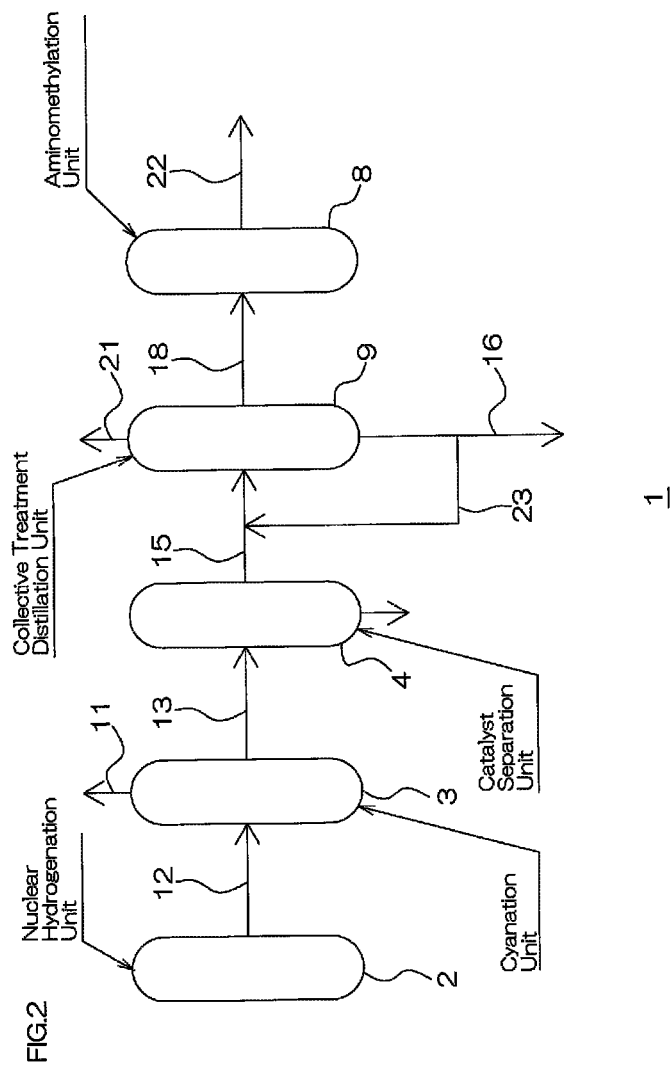
FIG. 2 is a schematic diagram illustrating another embodiment of a plant in which the method for producing trans-bis(aminomethyl)cyclohexane of the present invention is used.

In FIG. 2, a plant 1 includes a nuclear hydrogenation unit 2, a cyanation unit 3, a catalyst separation unit 4, a collective treatment distillation unit 9, and an aminomethylation unit 8.

In the plant 1, the mixture (mixture containing dicyanocyclohexane and high boiling point component) from which the catalyst is separated in the catalyst separation unit 4 is taken out from the catalyst separation unit 4 through the transport line 15, and is fed to the collective treatment distillation unit 9.

The collective treatment distillation unit 9 is a known distillation column, and is provided as a unit for separating the high boiling point component, and separating trans isomer from the above-described mixture, and furthermore, isomerizing cis isomer into trans.

In the collective treatment distillation unit 9, by distilling the above-described mixture (including dicyanocyclohexane and high boiling point component), cis-dicyanocyclohexane in the mixture is isomerized into trans (trans-isomerization step). Furthermore, trans-dicyanocyclohexane is taken out from the column top of the distillation column (trans isomer separation step), and a tar component is taken out from the column bottom of the distillation column (high boiling point component separation step).

The distillation conditions in the collective treatment distillation unit 9 are as follows: to be specific, distillation column has a column top temperature of, for example, 130° C. or more, preferably 140° C. or more, and for example, 220° C. or less, preferably 200° C. or less. The distillation column has a column bottom temperature of, for example, 200° C. or more, preferably 220° C. or more, and for example, 320° C. or less, preferably 300° C. or less.

The residence time at the column bottom is, for example, 1 hour or more, preferably 2 hours or more, and for example, 50 hours or less, preferably 25 hours or less.

When the distillation conditions are within the above-described range, the balance between the speed of isomerization of cis-dicyanocyclohexane into trans, and the speed of taking out trans-dicyanocyclohexane can be adjusted, and trans-dicyanocyclohexane can be separated efficiently.

In the distillation, high boiling point components (tar component) such as reaction intermediate used in the cyanation step and by-products are separated as column bottom components, and recovered through the discharge line 16.

Preferably, the high boiling point component (tar component) is taken out from the ejection line 23 branched from the discharge line 16 (ref: FIG. 1), and added (fed) to dicyanocyclohexane in the transport line 15.

In this manner, in the collective treatment distillation unit 9, cis-dicyanocyclohexane can be isomerized into trans in the presence of a tar component, and efficiency of isomerization of cis into trans can be improved.

The mixing ratio of the tar component relative to dicyanocyclohexane in the collective treatment distillation unit 9 is as follows: for example, 2 parts by mass or more, preferably 5 parts by mass or more, for example, 30 parts by mass or less, preferably 20 parts by mass or less of the tar component relative to 100 parts by mass of a total of dicyanocyclohexane.

By collectively treating the steps in the collective treatment distillation unit 9, isomerization into trans can be performed and trans isomer can be taken efficiently, and therefore production efficiency can be improved.

The produced trans-dicyanocyclohexane is fed to the aminomethylation unit 8 through the transport line 18 as described above to be subjected to aminomethylation. Trans-bis(aminomethyl)cyclohexane can be produced in this manner.

The thus produced trans-bis(aminomethyl)cyclohexane can be suitably used for example, in production of bis(isocyanatomethyl)cyclohexane without limitation.

In the method for producing bis(isocyanatomethyl)cyclohexane of the present invention, trans-bis(aminomethyl)cyclohexane produced by the above-described method for producing trans-bis(aminomethyl)cyclohexane is isocyanized.

Trans-bis(aminomethyl)cyclohexane is isocyanized by, for example, phosgenation of trans-bis(aminomethyl)cyclohexane (hereinafter may be referred to as phosgenation), or by carbamation of trans-bis(aminomethyl)cyclohexane, and thereafter, thermal decomposition (hereinafter may be referred to as carbamation.).

The phosgenation method can be performed, to be more specific, by a method (hereinafter may be referred to as cold/hot two-stage phosgenation method) in which trans-bis(aminomethyl)cyclohexane is directly allowed to react with phosgene; or a method (hereinafter may be referred to as amine hydrochloride phosgenation method) in which hydrochloride of trans-bis(aminomethyl)cyclohexane is suspended in an inert solvent (described later) to react with phosgene.

In the cold/hot two-stage phosgenation method, for example, first, an inert solvent is introduced to a reactor capable of stirring and provided with a phosgene inlet tube, and then the pressure in the reaction system is set to, for example, normal pressure to 1.0 MPa, preferably normal pressure to 0.5 MPa, and the temperature is set to, for example, 0 to 80° C. preferably 0 to 60° C.

Examples of inert solvents include aromatic hydrocarbons such as benzene, toluene, xylene, ethylbenzene, etc.; aliphatic acid esters such as ethyl acetate, butyl acetate, amyl acetate, etc.; aromatic carboxylic acid esters such as methyl salicylate, dimethyl phthalate, dibutyl phthalate, methyl benzoate, etc.; chlorinated aromatic hydrocarbons such as monochlorobenzene, orthodichlorobenzene, paradichlorobenzene, trichlorobenzene, etc.; and chlorinated hydrocarbons such as chloroform, carbon tetrachloride, etc.

These inert solvents may be used singly or in combination of two or more.

The blending amount (total amount) of the inert solvent relative to 100 parts by mass of trans-bis(aminomethyl)cyclohexane as a material is, for example, 400 to 3000 parts by mass, preferably 500 to 2000 parts by mass.

Next, in this method, phosgene is introduced, for example, so that the amount of phosgene is 1 to 10 times mol, preferably 1 to 6 times mol relative to one amino group in trans-bis(aminomethyl)cyclohexane; and trans-bis(aminomethyl)cyclohexane dissolved in the above-described inert solvent is added. During this time, the reaction liquid is kept at, for example, 0 to 80° C., preferably 0 to 60° C., and at the same time, generated hydrogen chloride is released outside of the reaction system via the reflux condenser (cold phosgenation reaction). The contents of the reactor are thus formed into a slurry.

In the cold phosgenation reaction, carbamoyl chloride compound and amine hydrochloride thereof are produced.

Next, in this method, the pressure in the reaction system is set to, for example, normal pressure to 1.0 MPa, preferably 0.05 to 0.5 MPa, and the temperature is increased for, for example, 30 min to 5 hours, to a temperature range of, for example, 80 to 180° C. After the temperature increase, for example, the reaction is allowed to continue for 30 min to 8 hours, thereby dissolving the slurry liquid completely (hot phosgenation reaction).

In the hot phosgenation reaction, at the time of temperature increase and the high temperature reaction, the dissolved phosgene is evaporated and escapes outside the reaction system via the reflux condenser, and therefore phosgene is introduced appropriately until the reflux amount from the reflux condenser can be confirmed.

After the termination of the hot phosgenation reaction, an inactive gas such as nitrogen gas is introduced into the reaction system at, for example, 80 to 180° C., preferably 90 to 160° C., thereby purging dissolved excessive phosgene and hydrogen chloride.

In the hot phosgenation reaction, carbamoyl chloride compound produced in the cold phosgenation reaction is thermally decomposed, bis(isocyanatomethyl)cyclohexane is produced, and furthermore, amine hydrochloride of trans-bis(aminomethyl)cyclohexane is phosgenated, thereby producing bis(isocyanatomethyl)cyclohexane.

On the other hand, in the phosgenation method of amine hydrochloride, first, hydrochloride of trans-bis(aminomethyl)cyclohexane is synthesized.

To be specific, for example, a reactor capable of stirring, and provided with a hydrochloric acid gas inlet tube, and a phosgene inlet tube is charged with an inert solvent and bis(aminomethyl)cyclohexane; the pressure in the reaction system is set to, for example, normal pressure to 1.0 MPa, preferably, normal pressure to 0.5 MPa; the temperature is set to, for example, 0 to 120° C., preferably 0 to 100° C. The inert solvent is blended in an amount (total amount) of, for example, 400 to 3000 parts by mass, preferably 500 to 2000 parts by mass relative to 100 parts by mass of material trans-bis(aminomethyl)cyclohexane.

Then, hydrochloric acid gas is introduced relative to 1 mol of the amino group of trans-bis(aminomethyl)cyclohexane, for example, 1 to 5 times mol, preferably 1 to 3 times mol. Hydrochloride of bis(aminomethyl)cyclohexane is synthesized in this manner.

Next, in this method, the reaction temperature is maintained at, for example, 80 to 180° C., preferably 90 to 160° C., and the reaction pressure is maintained at, for example, normal pressure to 1.0 MPa, preferably 0.05 to 0.5 MPa, and phosgene is introduced for 1 to 10 hours so that the total phosgene amount is 1 to 10 times the stoichiometric amount.

Bis(isocyanatomethyl)cyclohexane is synthesized in this manner.

The reaction progress can be assumed based on the amount of the hydrogen chloride gas generated, and when the undissolved slurry in the above-described inert solvent disappeared and the reaction liquid became clear and homogeneous. The generated hydrogen chloride is released, for example, outside the reaction system via the reflux condenser. At the time of reaction termination, the dissolved excessive phosgene and hydrogen chloride are purged by the above-described method. Thereafter, cooling is performed, and the inert solvent is distilled off under reduced pressure.

Examples of carbamation method include urea method.

In urea method, for example, first, carbamation of trans-bis(aminomethyl)cyclohexane is performed, thereby producing carbamate (bis(methoxycarbonylaminomethyl)cyclohexane).

To be more specific, as reaction materials, trans-bis(aminomethyl)cyclohexane, urea and/or N-non-substitute carbamate, and alcohol are allowed to react.

Examples of N-non-substitute carbamates include N-non-substitute carbamic acid aliphatic esters (e.g., methyl carbamate, ethyl carbamate, propyl carbamate, iso-propyl carbamate, butyl carbamate, iso-butyl carbamate, sec-butyl carbamate, tert-butyl carbamate, pentyl carbamate, iso-pentyl carbamate, sec-pentyl carbamate, hexyl carbamate, heptyl carbamate, octyl carbamate, 2-ethylhexyl carbamate, nonyl carbamate, decyl carbamate, isodecyl carbamate, dodecyl carbamate, tetradecyl carbamate, hexadecyl carbamate, etc.); and N-non-substitute carbamic acid aromatic esters (e.g., phenyl carbamate, tolyl carbamate, xylyl carbamate, biphenyl carbamate, naphthyl carbamate, anthryl carbamate, phenanthryl carbamate, etc.).

These N-non-substitute carbamates may be used singly or in combination of two or more.

As the N-non-substitute carbamate, preferably, N-non-substitute carbamic acid aliphatic esters are used.

Examples of alcohols include primary to tertiary monohydric alcohols, to be more specific, aliphatic alcohols and aromatic alcohols.

Examples of aliphatic alcohols include straight chain aliphatic alcohols (e.g., methanol, ethanol, n-propanol, n-butanol (1-butanol), n-pentanol, n-hexanol, n-heptanol, n-octanol (1-octanol), n-nonanol, n-decanol, n-dodecanol, n-tetradecanol, n-hexadecanol, etc.), and branched aliphatic alcohols (e.g., iso-propanol, iso-butanol, sec-butanol, tert-butanol, iso-pentanol, sec-pentanol, 2-ethylhexanol, iso-decanol, etc.).

Examples of aromatic alcohols include phenol, hydroxytoluene, hydroxyxylene, biphenylalcohol, naphthalenol, anthracenol, and phenanthrol.

These alcohols may be used singly or in combination of two or more.

As the alcohol, preferably, aliphatic alcohols, more preferably, straight chain aliphatic alcohols are used.

As the alcohol, preferably, above-described monohydric alcohols having 4 to 7 carbon atoms (straight chain monohydric alcohol having 4 to 7 carbon atoms, and branched monohydric alcohol having 4 to 7 carbon atoms) are used.

Then, in this method, trans-bis(aminomethyl)cyclohexane, urea and/or N-non-substitute carbamate, and alcohol are blended, and preferably, allowed to react in liquid phase.

The mixing ratio between the trans-bis(aminomethyl)cyclohexane, urea and/or N-non-substitute carbamate, and alcohol is not particularly limited, and can be selected suitably in a comparatively wide range.

Generally, the amount of urea and N-non-substitute carbamate blended, and the amount of alcohol blended are sufficient when they are equal in mol or more relative to the amino group of trans-bis(aminomethyl)cyclohexane, and therefore, urea and/or above-described N-non-substitute carbamate, alcohol themselves can be used as a reaction solvent in this reaction.

When urea and/or the above-described N-non-substitute carbamate, or alcohol are used also as the reaction solvent, as necessary, an excessive amount of urea and/or the above-described N-non-substitute carbamate, or alcohol are used, but with an overly excessive amount, consumption energy in the separation process after the reaction increases, and therefore industrially inappropriate.

Therefore, in view of improving the yield of carbamate, the amount of urea and/or above-described N-non-substitute carbamate blended is, relative to one amino group of trans-bis(aminomethyl)cyclohexane, 0.5 to 20 times mol, preferably 1 to 10 times mol, more preferably 1 to 5 times mol, and the amount of alcohol blended is, relative to one amino group of trans-bis(aminomethyl)cyclohexane, 0.5 to 100 times mol, preferably 1 to 20 times mol, and more preferably 1 to 10 times mol.

In this method, a catalyst can also be used.

The catalyst is not particularly limited, and examples thereof include: a first group (in conformity with IUPAC Periodic Table of the Elements (version date 22 Jun. 2007). The same applies in the following.) metal compound (e.g., lithium methanolate, lithium ethanolate, lithium propanolato, lithium butanolato, sodium methanolate, potassium-tert-butanolato, etc.), a second group metal compound (e.g., magnesium methanolate, calcium methanolate, etc.), a third group metal compound (e.g., cerium (IV) oxide, uranyl acetate, etc.), a fourth group metal compound (titaniumtetraisopropanolato, titaniumtetrabutanolato, titanium tetrachloride, titaniumtetraphenolate, titanium naphthate, etc.), a fifth group metal compound (e.g., vanadium (III) chloride, vanadium acetylacetonate, etc.), a sixth group metal compound (e.g., chromium (III) chloride, molybdenum (VI) oxide, molybdenum acetyl acetonate, tungsten (VI) oxide, etc.), a seventh group metal compound (e.g., manganese (II) chloride, manganese (II) acetate, manganese (III) acetate, etc.), an eighth group metal compound (e.g., iron (II) acetate, iron (III) acetate, iron phosphate, iron oxalate, ferric (III) chloride, iron (III) bromide, etc.), a ninth group metal compound (e.g., cobalt acetate, cobalt chloride, cobalt sulfurate, cobalt naphthenate, etc.), a tenth group metal compound (e.g., nickel chloride, nickel acetate, nickel naphthenate, etc.), an eleventh group metal compound (e.g., copper (II) acetate, copper (II) sulfate, copper (II) nitrate, bis-(triphenyl-phosphineoxide)-copper (II) chroride, copper molybdate, silver acetate, gold acetate, etc.), a twelfth group metal compound (e.g., zinc oxide, zinc chloride, zinc acetate, zinc acetonyl acetate, zinc octanoate, zinc oxalate, zinc hexylate, zinc benzoate, zinc undecylate, etc.), a thirteen group metal compound (e.g., aluminum acetyl acetonate, aluminum-isobutyrate, aluminum trichloride, etc.), a fourteen group metal compound (e.g., tin (II) chloride, tin (IV) chloride, lead acetate, lead phosphate, etc.), and a fifteenth group metal compound (e.g., antimony (III) chloride, antimony (V) chloride, bismuth (III) chloride, etc.).

Examples of catalysts also include $Zn(OSO_2CF_3)_2$ (also indicated as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2CH_5)_2$, $Zn(BF_4)_2$, $Zn(PF_6)_2$, $Hf(OTf)_4$ (hafnium trifluoromethanesulfonate, $Sn(OTf)_2$, $Al(OTf)_3$, and $Cu(OTf)_2$.

These catalysts may be used singly or in combination of two or more.

The blending amount of the catalyst relative to 1 mol of trans-bis(aminomethyl)cyclohexane is, for example, 0.000001 to 0.1 mol, preferably 0.00005 to 0.05 mol. When the blending amount of the catalyst is more than such a range, no additional significant reaction facilitating effects can be seen, and at the same time, the increase in the blending amount may increase costs. On the other hand, when the blending amount is smaller than such a range, reaction facilitating effects may not be obtained.

The catalyst may be added all at once, continuously, or dividedly and intermittently several times, any of which does not affect reaction activity, and is not limited.

In this reaction, the reaction solvent is not necessarily needed, but when the reaction materials are solid, or when reaction product deposits, for example, a solvent may be blended, which improves handleability.

Examples of solvents is not particularly limited as long as the solvent is inert or low in reactivity relative to the reaction materials, i.e., trans-bis(aminomethyl)cyclohexane, urea and/or N-non-substitute carbamate, and alcohol, and to the reaction product, i.e., a urethane compound, and examples thereof include aliphatic hydrocarbons (e.g., hexane, pentane, petroleum ether, ligroin, cyclododecane, decalin, etc.), aromatic hydrocarbons (e.g., benzene, toluene, xylene, ethylbenzene, isopropylbenzene, butylbenzene, cyclohexylbenzene, tetralin, chlorobenzene, o-dichlorobenzene, methylnaphthalene, chloronaphthalene, dibenzyltoluene, triphenylmethane, phenylnaphthalene, biphenyl, diethylbiphenyl, triethylbiphenyl, etc.), ethers (e.g., diethylether, diisopropylether, dibutylether, anisole, diphenylether, tetrahydrofuran, ethylene glycol dimethyl ether, ethylene glycol diethyl ether, ethylene glycol dibutyl ether, diethylene glycol dimethyl ether, diethylene glycol diethyl ether, etc.), carbonates (e.g., dimethylcarbonate, diethylcarbonate, dipropylcarbonate, dibutylcarbonate, etc.), nitriles (e.g., acetonitrile, propionitrile, adiponitrile, benzonitrile, etc.), aliphatic halogenated hydrocarbons (e.g., methylene chloride, chloroform, 1,2-dichloroethane, 1,2-dichloropropane, 1,4-dichlorobutane, etc.), amides (e.g., dimethylformamide, dimethylacetamide, etc.), nitro compounds (e.g., nitromethane, nitrobenzene, etc.), N-methyl pyrrolidinone, N,N-dimethylimidazolidinone, and dimethyl sulfoxide.

Of these reaction solvents, in view of economy, and handleability, etc., aliphatic hydrocarbons and aromatic hydrocarbons are used preferably.

Such a reaction solvent may be used singly or in combination of two or more.

The blending amount of the reaction solvent is not particularly limited as long as the amount is an amount that allows the target product, i.e., carbamate (bis(methoxycarbonylaminomethyl)cyclohexane) to dissolve. However, the blending amount of the reaction solvent is preferably small as much as possible because of the following reasons: industrially, the reaction solvent has to be collected from the reaction liquid, and therefore the energy consumed for the collection is to be decreased as much as possible, and also when the blending amount is large, the reactant concentration is decreased and the reaction rate is decreased. To be more specific, the blending amount of the reaction solvent relative to 1 part by mass of trans-bis(aminomethyl)cyclohexane is, usually in the range of 0.1 to 500 parts by mass, preferably 1 to 100 parts by mass.

In this reaction, the reaction temperature is suitably selected in the range of, for example, 100 to 350° C., preferably 150 to 300° C. The reaction temperature lower than these may reduce the reaction rate, meanwhile, the reaction temperature higher than these may decrease the yield of the target product, carbamate (bis(methoxycarbonylaminomethyl)cyclohexane) with increase of side reactions.

The reaction pressure is usually atmospheric pressure, but when the boiling point of components in the reaction liquid is lower than the reaction temperature, the pressure may be increased, or as necessary, decreased.

The reaction time is, for example, 0.1 to 20 hours, preferably 0.5 to 10 hours. The reaction time shorter than these may decrease the yield of the target product, carbamate (bis(methoxycarbonylaminomethyl)cyclohexane). On the other hand, the reaction time longer than such a range is inappropriate in view of industrial production.

The reaction can be performed, for example, by charging a reaction vessel with trans-bis(aminomethyl)cyclohexane, urea and/or N-non-substitute carbamate, alcohol, and as necessary a catalyst and a reaction solvent under the above-described conditions, and stirring or mixing the mixture. In this manner, carbamate (bis(methoxycarbonylaminomethyl) cyclohexane) is produced under mild conditions, for a short period of time, low costs, and high yield.

The produced carbamate (bis(methoxycarbonylaminomethyl)cyclohexane) correspond generally to the above-described trans-bis(aminomethyl)cyclohexane used as the material component, and to be more specific, when trans-1,3-bis(aminomethyl)cyclohexane is used as the material component, 1,3-bis(methoxycarbonylaminomethyl)cyclohexane is obtained, and when trans-1,4-bis(aminomethyl) cyclohexane is used as the material component, 1,4-bis (methoxycarbonylaminomethyl)cyclohexane is produced.

In this reaction, ammonia is produced as a by-product.

In this reaction, when N-non-substitute carbamate is blended, and alcohol corresponding to its ester is produced as a by-product.

In this reaction, the reaction type can be any of batch processing and continuous processing.

In this reaction, preferably, reaction is conducted while ammonia produced as a by-product is discharged. Furthermore, when N-non-substitute carbamate is blended, reaction is conducted while discharging the alcohol produced as a by-product.

In this manner, production of the target product, i.e., carbamate (bis(methoxycarbonylaminomethyl)cyclohexane) can be promoted, and the yield can be improved even more.

When the obtained carbamate (bis(methoxycarbonylaminomethyl)cyclohexane) is isolated, for example, carbamate (bis(methoxycarbonylaminomethyl)cyclohexane) may be separated from the reaction liquid including excessive (unreacted) urea and/or N-non-substitute carbamate, excessive (unreacted) alcohol, catalyst, carbamate (bis(methoxycarbonylaminomethyl)cyclohexane), reaction solvent, ammonia produced as a by-product, alcohol produced as a by-product depending on the case, by a known separation purifying method.

Then, in the method for producing bis(isocyanatomethyl) cyclohexane, the produced carbamate (bis(methoxycarbonylaminomethyl)cyclohexane) as described above is thermally decomposed, thus producing bis(isocyanatomethyl) cyclohexane, and alcohol as by-product.

The produced bis(isocyanatomethyl)cyclohexane generally corresponds to the above-described trans-bis(aminomethyl)cyclohexane used as the material component, to be more specific, when trans-1,3-bis(aminomethyl)cyclohexane is used as the material component, 1,3-bis(isocyanatomethyl)cyclohexane is produced, and when trans-1,4-bis(aminomethyl)cyclohexane is used as the material component, 1,4-bis(isocyanatomethyl)cyclohexane is produced.

As the alcohol, usually, alcohol that is the same type with the alcohol used as the material component is produced as a by-product.

The thermal decomposition is not particularly limited, for example, and a known decomposition method such as liquid phase method and gas phase method may be used.

In the gas phase method, bis(isocyanatomethyl)cyclohexane and alcohol produced by thermal decomposition can be separated from the gaseous product mixture by fractional condensation. In the liquid phase method, bis(isocyanatomethyl)cyclohexane and alcohol produced by thermal decomposition can be separated, for example, by distillation, or by using a solvent and/or an inactive gas as a support substance.

As the thermal decomposition, preferably, in view of workability, liquid phase method is used.

The thermal decomposition reaction of carbamate (bis (methoxycarbonylaminomethyl)cyclohexane) in the liquid phase method is reversible reaction, and thus preferably, in order to suppress reverse reaction (urethane reaction between (bis(isocyanatomethyl)cyclohexane and alcohol) of thermal decomposition reaction, carbamate (bis(methoxycarbonylaminomethyl)cyclohexane) is subjected to thermal decomposition, and at the same time, bis(isocyanatomethyl) cyclohexane, and/or alcohol produced as a by-product are, for example, discharged as gases from the reaction mixture, and then these are separated.

Reaction conditions of thermal decomposition reaction are as follows: preferably, carbamate (bis(methoxycarbonylaminomethyl)cyclohexane) is excellently thermally decomposed; bis(isocyanatomethyl)cyclohexane and alcohol produced in the thermal decomposition are evaporated, thereby avoiding equilibrium state of carbamate (bis (methoxycarbonylaminomethyl)cyclohexane) and bis(isocyanatomethyl)cyclohexane; and further suppressing side reactions such as polymerization of bis(isocyanatomethyl) cyclohexane.

As such reaction conditions, to be more specific, the thermal decomposition temperature is usually 350° C. or less, preferably 80 to 350° C., more preferably 100 to 300° C. When the thermal decomposition temperature is lower than 80° C., a practical reaction rate may not be achieved, and when the thermal decomposition temperature is more than 350° C., unfavorable side reactions such as polymerization of bis(isocyanatomethyl)cyclohexane may be caused. The pressure at the time of thermal decomposition reaction is preferably a pressure that allows the produced alcohol to be evaporated relative to the above-described thermal decomposition reaction temperature, and in view of equipment and application, practically, preferably is 0.133 to 90 kPa.

Carbamate (bis(methoxycarbonylaminomethyl)cyclohexane) used in the thermal decomposition may be purified one. Alternatively, using a crude material of carbamate (bis(methoxycarbonylaminomethyl)cyclohexane) obtained by collecting excessive (unreacted) urea and/or N-non-substitute carbamate, excessive (unreacted) alcohol, catalyst, reaction solvent, ammonia produced as a by-product, and alcohol produced as a by-product depending on the case after the termination of the above-described reaction (that is, reaction between trans-bis(aminomethyl)cyclohexane, urea and/or N-non-substitute carbamate, and alcohol) and separating it therefrom, the thermal decomposition may be conducted afterwards.

Furthermore, as necessary, a catalyst and an inert solvent may be added. These catalyst and inert solvent may be added, although depending on the types of these, at any of the time of above-described reaction, before and after the distillation separation after the reaction, and before and after the separation of carbamate (bis(methoxycarbonylaminomethyl)cyclohexane).

As the catalyst used in the thermal decomposition, one or more metal substance selected from Sn, Sb, Fe, Co, Ni, Cu, Zn, Cr, Ti, Pb, Mo, and Mn; or a metal compound such as oxide, halide, carboxylate, phosphate, and an organic metal compound of these used in urethane reaction between isocyanate and hydroxyl groups is used. Of these examples of catalysts, because Fe, Sn, Co, Sb, and Mn exhibit effects of suppressing by-products, they are preferably used.

Examples of metal catalysts of Sn include tin oxide, tin chloride, tin bromide, tin iodide, tin formate, tin acetate, tin oxalate, tin octylate, tin stearate, tin oleate, tin phosphate, dibutyltin dichloride, dibutyltin dilaurate, and 1,1,3,3-tetrabutyl-1,3-dilauryloxydistannoxane.

Examples of metal catalysts of Fe, Co, Sb, and Mn include acetate, benzoate, naphthenate, and acetylacetonato salt thereof.

The blending amount of the catalyst (metal substance or a compound thereof) relative to the reaction liquid is in the range of 0.0001 to 5 mass %, preferably in the range of 0.001 to 1 mass %.

The inert solvent is not particularly limited, as long as the inert solvent at least dissolves carbamate (bis(methoxycarbonylaminomethyl)cyclohexane), is inert relative to carbamate (bis(methoxycarbonylaminomethyl)cyclohexane) and isocyanate, and is stable at the temperature of thermal decomposition. However, to perform thermal decomposition reaction efficiently, its boiling point is preferably higher than that of the produced isocyanate. Examples of inert solvents include esters such as dioctyl phthalate, didecyl phthalate, and didodecyl phthalate; and aromatic hydrocarbons and aliphatic hydrocarbons usually used as a heating medium such as dibenzyltoluene, triphenylmethane, phenylnaphthalene, biphenyl, diethylbiphenyl, and triethylbiphenyl.

The inert solvent can also be obtained from commercially available products, and examples thereof include Barrel process oil B-01 (aromatic hydrocarbons, boiling point: 176° C.), Barrel process oil B-03 (aromatic hydrocarbons, boiling point: 280° C.), Barrel process oil B-04AB (aromatic hydrocarbons, boiling point: 294° C.), Barrel process oil B-05 (aromatic hydrocarbons, boiling point: 302° C.). Barrel process oil B-27 (aromatic hydrocarbons, boiling point: 380° C.), Barrel process oil B-28AN (aromatic hydrocarbons, boiling point: 430° C.), Barrel process oil B-30 (aromatic hydrocarbons, boiling point: 380° C.), Barrel therm 200 (aromatic hydrocarbons, boiling point: 382° C.), Barrel therm 300 (aromatic hydrocarbons, boiling point: 344° C.), Barrel therm 400 (aromatic hydrocarbons, boiling point: 390° C.), Barrel therm 1H (aromatic hydrocarbons, boiling point: 215° C.), Barrel therm 2H (aromatic hydrocarbons, boiling point: 294° C.), Barrel therm 350 (aromatic hydrocarbons, boiling point: 302° C.), Barrel therm 470 (aromatic hydrocarbons, boiling point: 310° C.), Barrel therm PA (aromatic hydrocarbons, boiling point: 176° C.). Barrel therm 330 (aromatic hydrocarbons, boiling point: 257° C.). Barrel therm 430 (aromatic hydrocarbons, boiling point: 291° C.), (all manufactured by Matsumura Oil Co., Ltd.), NeoSK-OIL 1400 (aromatic hydrocarbons, boiling point: 391° C.). NeoSK-OIL 1300 (aromatic hydrocarbons, boiling point: 291° C.), NeoSK-OIL 330 (aromatic hydrocarbons, boiling point: 331° C.). NeoSK-OIL 170 (aromatic hydrocarbons, boiling point: 176° C.). NeoSK-OIL 240 (aromatic hydrocarbons, boiling point: 244° C.), KSK-OIL 260 (aromatic hydrocarbons, boiling point: 266° C.), and KSK-OIL 280 (aromatic hydrocarbons, boiling point: 303° C.), (all manufactured by Soken Technix's).

The blending amount of the inert solvent relative to 1 part by mass of carbamate (bis(methoxycarbonylaminomethyl)cyclohexane) is in a range of 0.001 to 100 parts by mass, preferably 0.01 to 80 parts by mass, and more preferably 0.1 to 50 parts by mass.

The thermal decomposition reaction can be conducted in any of the batch reaction, in which carbamate (bis(methoxycarbonylaminomethyl)cyclohexane), a catalyst, and an inert solvent are charged at once, and the continuous reaction, in which carbamate (bis(methoxycarbonylaminomethyl)cyclohexane) is charged in an inert solvent containing a catalyst under reduced pressure.

In the thermal decomposition, bis(isocyanatomethyl)cyclohexane and alcohol are produced, and at the same time, for example, allophanate, amines, urea, carbonate, carbamate, carbon dioxide, etc. may be produced by side reaction, and therefore as necessary, the obtained bis(isocyanatomethyl)cyclohexane is purified by a known method.

As the carbamation method, although not to be described in detail, in addition to the above-described urea method, a known carbonation method is also used: that is, a method in which carbamate (bis(methoxycarbonylaminomethyl)cyclohexane) is obtained by synthesizing carbamate (bis(methoxycarbonylaminomethyl)cyclohexane) from trans-bis(aminomethyl)cyclohexane, and dialkyl carbonate or diaryl carbonate, and thermally decomposing the carbamate (bis(methoxycarbonylaminomethyl)cyclohexane) in the same manner as described above.

In the method for producing bis(isocyanatomethyl)cyclohexane, trans-bis(aminomethyl)cyclohexane produced by the above-described method for producing trans-bis(aminomethyl)cyclohexane is used, and therefore bis(isocyanatomethyl)cyclohexane can be produced more efficiently.

In the bis(isocyanatomethyl)cyclohexane, the above-described method for producing bis(isocyanatomethyl)cyclohexane is used, and therefore can be produced efficiently.

The thus produced bis(isocyanatomethyl)cyclohexane of the present invention has a purity of, for example, 95 to 100 mass %, preferably 97 to 100 mass %, more preferably 98 to 100 mass %, particularly preferably 99 to 100 mass %, and most preferably 99.5 to 100 mass %.

To the bis(isocyanatomethyl)cyclohexane, for example, a stabilizer can also be added.

Examples of stabilizers include antioxidants, acid compounds, compounds containing sulfonamide groups, and organic phosphite.

Examples of antioxidants include hindered phenolic antioxidants, and specific examples include 2,6-di(t-butyl)-4-methylphenol, 2,4,6-tri-t-butylphenol, 2,2'-methylenebis-(4-methyl-6-t-butylphenol), 2,2'-thio-bis-(4-methyl-6-t-butylphenol), 4,4'-thio-bis(3-methyl-6-t-butylphenol), 4,4'-butylidene-bis-(6-t-butyl-3-methylphenol), 4,4'-methylidene-bis-(2,6-di-t-butylphenol), 2,2'-methylene-bis-[4-methyl-6-(1-methylcyclohexyl)-phenol], tetrakis-[methylene-3-(3,5-di-t-butyl-4-hydroxyphenyl)-propionyl]-methane, 1,3,5-trimethyl-2,4,6-tris-(3,5-di-t-butyl-4-hydroxyphenyl)-propionyl-methane, 1,3,5-trimethyl-2,4,6-tris-(3,5-di-t-butyl-4-hydroxybenzyl)-benzene, N,N'-hexamethylene-bis-(3,5-di-t-butyl-4-hydroxyhydrocinnamic acid amide, 1,3,5-tris-(3,5-di-t-butyl-4-hydroxybenzyl)-isocyanurate, 1,1,3-tris-(5-t-butyl-4-hydroxy-2-methylphenyl)-butane, 1,3,5-tris-(3,5-di-t- butyl-4-hydroxybenzyl)-mesitylene, ethylene glycol-bis-[3,3-bis-(3'-t-butyl-4'-hydroxyphenyl)-butyrate, 2,2'-thiodiethyl-bis-3-(3,5-di-t-butyl-4-hydroxyphenyl)-propionate, di-(3-t-butyl-4'-hydroxy-5-methylphenyl)-dicyclopentadiene, 2,2'-methylene-bis-(4-methyl-6-cyclohexylphenol), 1,6-hexanediol-bis-(3,5-di-t-butyl-4-hydroxyphenyl)-propionate, 2,4-bis-(n-octylthio)-6-(4-hydroxy-3,5-di-t-butylanilino)-1,3,5-triazine, diethyl-3,5-di-t-butyl-4-hydroxybenzylphosphonate, triethylene glycol-bis-3-(t-butyl-4-hydroxy-5-methylphenyl)-propionate, and also include, for example, IRGANOX 1010, IRGANOX 1076, IRGANOX 1098, IRGANOX 1135, IRGANOX 1726, IRGANOX 245, IRGANOX 3114, and IRGANOX 3790 (all manufactured by BASF Japan Ltd., trade name).

These antioxidants may be used singly or in combination of two or more.

Examples of acid compounds include organic acid compounds, to be specific, phosphate, phosphite, hypophosphite, formic acid, acetic acid, propionic acid, hydroxyacetic acid, oxalic acid, lactic acid, citric acid, malic acid, sulfonic acid, sulfonate, phenol, enol, imide, and oxime.

These acid compounds may be used singly or in combination of two or more.

Examples of compounds containing sulfonamide groups include aromatic sulfonamides and aliphatic sulfonamides.

Examples of aromatic sulfonamides include benzene sulfonamide, dimethylbenzene sulfonamide, sulfanilamide, o- and p-toluene sulfonamide, hydroxynaphthalene sulfonamide, naphthalene-1-sulfonamide, naphthalene-2-sulfonamide, m-nitrobenzene sulfonamide, and p-chlorobenzene sulfonamide.

Examples of aliphatic sulfonamides include methane sulfonamide, N,N-dimethylmethane sulfonamide, N,N-dimethylethane sulfonamide, N,N-diethylmethane sulfonamide, N-methoxymethane sulfonamide, N-dodecylmethane sulfonamide, N-cyclohexyl-1-butanesulfonamide, and 2-aminoethane sulfonamide.

These compounds containing sulfonamide groups may be used singly or in combination of two or more.

Examples of organic phosphorous acid esters include organic phosphorous acid diester, and organic phosphorous acid triester, to be more specific, for example, monophosphites such as triethyl phosphite, tributyl phosphite, tris (2-ethylhexyl) phosphite, tridecyl phosphite, trilauryl phosphite, tris (tridecyl) phosphite, tristearyl phosphite, triphenyl phosphite, tris (nonylphenyl) phosphite, tris (2,4-di-t-butylphenyl) phosphite, diphenyldecyl phosphite, and diphenyl (tridecyl) phosphite; di, tri, or tetra phosphites derived from polyhydric alcohol such as distearyl•pentaerythrityl•diphosphite, di•dodecyl•pentaerythritol•diphosphite, di•tridecyl•pentaerythritol•diphosphite, dinonylphenyl•pentaerythritol•diphosphite, tetraphenyl•tetra•tridecyl•pentaerythrityl•tetra phosphite, tetraphenyl•dipropylene glycol•diphosphite, and tripentaerythritol•tri phosphite; and diphosphites derived from bisphenol compounds such as di•alkyl•bisphenol A•diphosphite having 1 to 20 carbons, and 4,4'-butylidene-bis(3-methyl-6-t-butylphenyl-di•tridecyl) phosphite; poly phosphites such as hydrogenated bisphenol A phosphite polymers (molecular weight 2400 to 3000); and tris (2,3-dichloropropyl) phosphate.

These organic phosphites may be used singly or in combination of two or more.

As the stabilizer, preferably, antioxidants, acid compounds, or a compound containing a sulfonamide group is used. More preferably, bis(isocyanatomethyl)cyclohexane is blended with an antioxidant, an acid compound and/or a compound containing a sulfonamide group.

By adding these stabilizers, storage stability of the isocyanate-modified product (described later) produced by using bis(isocyanatomethyl)cyclohexane can be improved.

The mixing ratio of the stabilizer is not particularly limited, and is appropriately selected according to necessity and its application.

To be specific, the mixing ratio of the antioxidant relative to 100 parts by mass of bis(isocyanatomethyl)cyclohexane is, for example, 0.0005 to 0.05 parts by mass.

The mixing ratio (when used in combination, a total thereof) of the acid compound and/or the compound containing the sulfonamide group relative to 100 parts by mass of bis(isocyanatomethyl)cyclohexane is, for example, 0.0005 to 0.02 parts by mass.

In the present invention, a polyisocyanate composition is further included.

The polyisocyanate composition is produced, to be more specific, by modifying bis(isocyanatomethyl)cyclohexane, and contains at least one functional group of (a) to (e) below.
(a) an isocyanurate group,
(b) an allophanate group,
(c) a biuret group,
(d) a urethane group, and
(e) a urea group.

The polyisocyanate composition containing the functional group (isocyanurate group) of the above-described (a) is a trimer of bis(isocyanatomethyl)cyclohexane, and for example, can be produced by allowing bis(isocyanatomethyl)cyclohexane to react in the presence of a known isocyanurattion catalyst to trimerize.

The polyisocyanate composition containing the functional group (allophanate group) of the above-described (b) is allophanate-modified bis(isocyanatomethyl)cyclohexane, and for example, can be produced by allowing bis(isocyanatomethyl)cyclohexane to react with monoalcohol, and then further allowing to react in the presence of a known allophanation catalyst.

The polyisocyanate composition containing the functional group (biuret group) of the above-described (c) is biuret-modified bis(isocyanatomethyl)cyclohexane, and for example, can be produced by allowing bis(isocyanatomethyl)cyclohexane to react with, for example, water, tertiary alcohol (e.g., t-butylalcohol, etc.), and secondary amine (e.g., dimethylamine, diethylamine, etc.), and then further allowing to react in the presence of a known biuretizing catalyst.

The polyisocyanate composition containing the functional group (urethane group) of the above-described (d) is a polyol-modified bis(isocyanatomethyl)cyclohexane, and for example, can be produced by allowing bis(isocyanatomethyl)cyclohexane to react with the polyol component (e.g., trimethylolpropane etc. To be specific, described later).

The polyisocyanate composition containing the functional group (urea group) of the above-described (e) is a polyamine-modified bis(isocyanatomethyl)cyclohexane, and can be produced by allowing bis(isocyanatomethyl) cyclohexane to react with water, and the polyamine component (described later).

The polyisocyanate composition containing at least one of the functional groups of the above-described (a) to (e) is sufficient, and can contain two or more of the functional groups of the above-described (a) to (e). Such a polyisocyanate composition is produced by suitably combining the above-described reactions.

For the polyisocyanate composition, preferably, a trimer (polyisocyanate composition containing isocyanurate group) of bis(isocyanatomethyl)cyclohexane is used.

The trimer of bis(isocyanatomethyl)cyclohexane further contains, in addition to the isocyanurate group, polyisocyanate having iminooxadiazinedione group.

In the polyisocyanate composition, the above-described bis(isocyanatomethyl)cyclohexane is used, and therefore can be produced more efficiently.

Then, by allowing the above-described bis(isocyanatomethyl)cyclohexane, and/or the above-described polyisocyanate composition, and the active hydrogen compound to react, polyurethane resin can be produced.

Examples of the active hydrogen compound include a polyol component, and a polyamine component, and preferably, a polyol component is used.

Examples of the polyol component include a low molecular-weight polyol and a high molecular weight polyol.

Low-molecular-weight polyols are compounds having two or more hydroxyl groups and a number average molecular weight of below 400, and examples thereof include dihydric alcohols such as ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, 3-methyl-1,5-pentanediol, 2,2,2-trimethylpentanediol, 3,3-dimethylolheptane, alkane (C7 to 20) diol, 1,3- or 1,4-cyclohexanedimethanol and a mixture thereof, 1,3- or 1,4-cyclohexanediol and a mixture thereof, hydrogenated bisphenol A, 1,4-dihydroxy-2-butene, 2,6-dimethyl-1-octene-3, 8-diol, bisphenol A, diethylene glycol, triethylene glycol, and dipropylene glycol; trihydric alcohols such as glycerin, and trimethylolpropane; tetrahydric alcohols such as tetramethylolmethane (pentaerythritol), and diglycerol; pentahydric alcohol such as xylitol: hexahydric alcohols such as sorbitol, mannitol, allitol, iditol, dulcitol, altritol, inositol, and dipentaerythritol; heptahydric alcohol such as perseitol; and octahydric alcohols such as sucrose.

These low-molecular-weight polyols may be used singly or in combination of two or more.

High molecular weight polyols are compounds having two or more hydroxyl groups and having a number average molecular weight of 400 or more, and examples thereof include polyetherpolyol (e.g., polyethylene glycol, polypropylene glycol, polytetramethylene ether glycol, etc.), polyesterpolyol, polycarbonatepolyol, polyurethane polyol, epoxypolyol, vegetable oil polyol, polyolefin polyol, acrylic polyol, vinyl monomer-modified polyol, and preferably, polyether polyol, polyester polyol, and polycarbonate polyol are used.

These polyol components may be used singly or in combination of two or more.

In this method, as necessary, known additives, for example, urethanizing catalysts including amines, organometallic compound, and potassium salt; and furthermore, plasticizer, anti-blocking agent, heat-resistant stabilizer, light stabilizer, antioxidant, releasing agent, pigment, dye, lubricant, filler, hydrolysis inhibitor can be added. These additives may be added during synthesis of each component or may be added during mixing and dissolving of each component, and further, they can also be added after synthesis.

In this method, polyurethane resin can be produced, for example, by using a known method such as one shot process, and prepolymer process, and subjecting the above-described bis(isocyanatomethyl)cyclohexane and/or the above-described polyisocyanate composition, and the active hydrogen compound to polymerization reaction, by polymerization method such as bulk polymerization or solution polymerization. The mixing formulation and the reaction conditions of the components are set suitably in accordance with the purpose and application.

In the polyurethane resin, the above-described bis(isocyanatomethyl)cyclohexane and the above-described polyisocyanate composition are used as the material component, and furthermore, the polyurethane resin is excellent in various physical properties.

Therefore, the polyurethane resin of the present invention can be used as, for example, coating, adhesive, sealant, thermoplastic, thermosetting elastomer, millable type, spandex (particularly, melt spinning spandex), ultraviolet ray cured polyurethane, polyurethane foam, microcellular, artificial or synthetic leather. To be more specific, for example, the polyurethane resin of the present invention can be used in variety of application such as sanitary materials including disposable diapers and sanitary napkins, for example, medical materials including operation apparel, bandages, wound protection film, gloves, for example, wrapping materials such as food packing materials, and furthermore, evewear materials, sports apparel materials, and tent materials.

EXAMPLES

Hereinafter, the present invention will be described more specifically with reference to Examples and Comparative Examples. However, the present invention is not limited to those Examples. The values shown in Examples can be replaced with the values shown in the embodiments (that is, upper limit value or lower limit value). The analysis was performed with gas chromatography.

Example 1

Step 1: Cyanation Step

A 3 L flask equipped with a stirrer, a thermometer, a gas inlet tube, a gas discharge pipe, and a gas cooling device was charged with 1400 parts by mass of a commercially available 1,4-cyclohexanedicarboxylic acid, 600 parts by mass of N,N'-dimethylimidazolidinone, and 17.6 parts by mass of tin oxide (II), and the mixture was heated to 170° C. Thereafter, ammonia gas was allowed to pass through at 1760 mL/min while stirring at 500 rpm, the temperature was raised to 280° C., and the temperature was kept to be constant: the reaction was performed for 14 hours. After the termination of the reaction, the mixture was cooled to 150° C., and hot filtration was performed to remove the solids. As a result of the analysis on the filtrate, the 1,4-cyclohexanedicarboxylic acid conversion rate was 100%, the 1,4-dicyanocyclohexane yield was 90.2%, the trans isomer ratio was 52%, and the N,N'-dimethylimidazolidinone concentration was 6.9 mass %.

Step 2: High Boiling Point Component Separation Step (1)

A 500 mL flask equipped with a stirrer, a thermometer, a gas discharge pipe, and a gas cooling device was charged with 370 parts by mass of the filtrate containing 1,4-dicyanocyclohexane produced in the above-described step 1: cyanation step, and the mixture was heated under the conditions of the following: a pressure of 4 kPa, a condenser refrigerant temperature of (column top temperature) 140° C., and a flask internal temperature of (column bottom temperature) 190 to 230° C. The condensate was distilled with a gas cooling device to 90 mass % relative to the charged amount (flask residence time (residence time at the column bottom) 4 hours), thereby producing a distillate.

As a result of analysis on the distillate, it was found that the 1,4-dicyanocyclohexane yield was 94.9% relative to the charged amount, and its trans isomer ratio was 54%. The tank bottom (residue) had a 1,4-dicyanocyclohexane concentration of 43.4 mass % and a trans isomer ratio of 38%.

Step 3: Trans Isomer Separation Step (1)

A 500 mL flask equipped with a stirrer, a thermometer, a gas discharge pipe, and a packed column (packing: Sulzer pack, theoretical plate number: 10) with a reflux device was charged with 300 parts by mass of the distillate obtained in the above-described high boiling point component separation step (1), and the distillate was distilled to 45 mass % relative to the charged amount (flask residence time (residence time at the column bottom) 5 hours) under the conditions of the following: a column top pressure of 6.7 kPa, a condenser refrigerant temperature of (column top temperature) 140° C., a flask internal temperature (column bottom temperature) of 230° C., and a reflux ratio of 1, thereby producing fractions. As a result of analysis on the fractions, it was found that a total of 1,4-dicyanocyclohexane having a trans isomer ratio of 90% or more was 37.5 mass % relative to the charged amount, the 1,4-dicyanocyclohexane yield was 41.5%, and the average trans isomer ratio was 92%. The tank bottom (residue) had a 1,4-dicyanocyclohexane concentration of 96.4 mass % and a trans isomer ratio of 28%.

Step 4: Trans-Isomerization Step

A 500 mL flask equipped with a stirrer, a thermometer, a gas discharge pipe, and a gas cooling device was charged with 145 parts by mass of the tank bottom obtained in the above-described step 3: the trans isomer separation step (1), and 30 parts by mass of the tank bottom obtained in the above-described step 2: high boiling point component separation step (1), and the mixture was heated at 280° C. for 4 hours. As a result of analysis on the reaction solution, it was found that the trans isomer ratio was 48%.

Step 5: High Boiling Point Component Separation Step (2)

Furthermore, the flask of the above-described step 4 was charged with 175 parts by mass of the filtrate obtained in the cyanation step of step 1, and the mixture was heated at a flask internal temperature (column bottom temperature) of 190 to 230° C., a pressure of 4 kPa, a condenser refrigerant temperature (column top temperature) of 140° C. The condensate was distilled with a gas cooling device to 85 mass % relative to the charged amount (flask residence time (residence time at the column bottom) 4 hours), thereby producing a distillate.

As a result of analysis on the distillate, it was found that the 1,4-dicyanocyclohexane yield was 91.0% relative to the charged amount, and its trans isomer ratio was 52%. The tank bottom had a 1,4-dicyanocyclohexane concentration of 50.1 mass % and a trans isomer ratio of 44%.

Step 6: Trans Isomer Separation Step (2)

A 500 mL flask equipped with a stirrer, a thermometer, a gas discharge pipe, and a packed column (packing: Sulzer pack, theoretical plate number: 10) with a reflux device was charged with 280 parts by mass of the distillate obtained in the above-described trans-isomerization step, and was distilled to 45 mass % relative to the charged amount (flask residence time (residence time at the column bottom) 5 hours) under the conditions below: a column top pressure of 6.7 kPa, a column top condenser refrigerant temperature (column top temperature) of 140° C., a flask internal temperature (column bottom temperature) of 230° C., and a reflux ratio of 1, thereby producing fractions. As a result of analysis on the fractions, it was found that a total of 1,4-dicyanocyclohexane having a trans isomer ratio of 90% or more was 41.0 mass % relative to the charged amount, the 1,4-dicyanocyclohexane yield was 44.2%, and the average trans isomer ratio was 93%. The tank bottom had a trans isomer ratio of 24%.

Step 7: Aminomethylation Step

A 1 L stainless steel reactor equipped with a stirrer, a thermometer, and a gas inlet tube was charged with 140 parts by mass of a mixture (trans-1,4-dicyanocyclohexane) of the fractions obtained in the trans isomer separation step (1) of step 3 and trans isomer separation step (2) of step 6, 14 parts by mass of a catalyst (manufactured by Kawaken Fine Chemicals Co., Ltd. Manganese-containing Raney cobalt), 156 mL of 28 mass % ammonia water, and 292 mL of 1-butanol, and the mixture was heated under normal pressure while stirring at 400 rpm to 80° C.

When the temperature reached 80° C., hydrogen was supplied intermittently so that the pressure was 0.95 MPa, and reaction was performed until there is no hydrogen absorption.

After the termination of the reaction, cooling was performed to room temperature, the reaction product was taken out, and the catalyst was removed by filtration.

The filtrate was analyzed, and it was found that the 1,4-dicyanocyclohexane conversion rate was 100%, the 1,4-bis(aminomethyl)cyclohexane yield was 96%, and its trans isomer ratio was 87%.

The reaction solution was subjected to distillation under reduced pressure at 1.3 kPa, thereby producing a 97% yield of 1,4-bis(aminomethyl)cyclohexane having a purity of 99.5% or more and a trans isomer ratio of 88%.

Step 8: Isocyanization Step

A 1.5 L stainless steel reactor equipped with a stirrer, a thermometer, a nitrogen inlet tube, a chlorine gas inlet tube, a phosgene inlet tube, a gas discharge pipe, a gas cooling device, and an automatic pressure regulating valve was charged with 55 parts by mass of 1,4-bis(aminomethyl) cyclohexane obtained in the above-described aminomethylation step, and 700 parts by mass of orthodichlorobenzene, and the mixture was heated while stirring at 300 rpm to 60° C. Thereafter, 1.2 mol of hydrochloric acid gas was introduced at a flow rate of 0.15 L/min. Cold water was allowed to go through the reactor jacket so that the internal temperature was kept to about 60 to 100° C.

Then, 77 parts by mass of phosgene was added thereto, and the pressure was increased to 0.2 MPa while the temperature of the reaction solution was increased to 150° C., and the reaction was further performed for 6 hours under a pressure of 0.2 MPa and a reaction temperature of 150° C. while adding phosgene. The phosgene added during the reaction was 230 parts by mass.

After the termination of the reaction, nitrogen gas was allowed to pass through at 100 to 150° C. at 0.4 L/min to degass. The solvent orthodichlorobenzene was distilled off under reduced pressure, and further distillation was performed under reduced pressure, thereby producing a 90% yield of 1,4-bis(isocyanatomethyl)cyclohexane having a purity of 99.5% or more and a trans isomer ratio of 86%.

Example 2

Step 4: Trans-Isomerization Step

A 500 mL flask equipped with a stirrer, a thermometer, a gas discharge pipe, and a gas cooling device was charged with 172 parts by mass of the tank bottom produced in trans isomer separation step (1) of step 3 of the above-described Example 1, and 3 parts by mass of the tank bottom obtained in the high boiling point component separation step of step 2 of Example 1, and heating was performed at 320° C. for 50 hours. As a result of analysis on the reaction solution, it was found that the trans isomer ratio was 45%.

Step 5: High Boiling Point Component Separation Step (2)

Furthermore, the above-described flask was charged with 175 parts by mass of the filtrate obtained in the cyanation step of step 1 in Example 1, heated at a pressure of 4 kPa, a condenser refrigerant temperature (column top temperature) of 140° C., and a flask internal temperature (column bottom temperature) of 190 to 230° C. The condensate was distilled with a gas cooling device to 85 mass % relative to the charged amount (flask residence time (residence time at the column bottom) 4 hours), thereby producing a distillate.

As a result of analysis on the distillate, it was found that the 1,4-dicyanocyclohexane yield was 88.7% relative to the charged amount, and its trans isomer ratio was 49%. The tank bottom had a 1,4-dicyanocyclohexane concentration of 68.3 mass % and a trans isomer ratio of 47%.

Step 6: Trans Isomer Separation Step (2)

A 500 mL flask equipped with a stirrer, a thermometer, a gas discharge pipe, and a packed column (packing: Sulzer pack, theoretical plate number: 10) equipped with a reflux device was charged with 280 parts by mass of the distillate obtained in the trans-isomerization step of the above-described step 4, and distilled to 45 mass % relative to the charged amount (flask residence time (residence time at the column bottom) 5 hours) with the conditions of the following: a column top pressure of 6.7 kPa, a column top condenser refrigerant temperature (column top temperature) of 140° C., a flask internal temperature (column bottom temperature) of 230° C., and a reflux ratio of 1, thereby producing fractions.

As a result of analysis on the fractions, it was found that a total of 1,4-dicyanocyclohexane having a trans isomer ratio of 90% or more was 41.0 mass % relative to the charged amount, the 1,4-dicyanocyclohexane yield was 43.6%, and the average trans isomer ratio was 92%. The tank bottom had a trans isomer ratio of 18%.

Step 7: Aminomethylation Step

A filtrate containing 1,4-bis(aminomethyl)cyclohexane was produced in the same manner as in the aminomethylation step in step 7 of Example 1 using the fraction produced as described above.

The filtrate was analyzed, and it was found that the 1,4-dicyanocyclohexane conversion rate was 100%, 1,4-bis (aminomethyl)cyclohexane yield was 97%, and its trans isomer ratio was 86%.

The reaction solution was subjected to distillation under reduced pressure at 1.3 kPa, thereby producing a 97% yield of 1,4-bis(aminomethyl)cyclohexane having a purity of 99.5% or more and a trans isomer ratio of 87%.

Example 3

Step 4: Trans-Isomerization Step

A 500 mL flask equipped with a stirrer, a thermometer, a gas discharge pipe, and a gas cooling device was charged with 130 parts by mass of the tank bottom produced in trans isomer separation step (1) of step 3 of the above-described Example 1, and 45 parts by mass of the tank bottom produced in the high boiling point component separation step of step 2 of Example 1, and the mixture was heated at 280° C. for 3 hours. As a result of analysis on the reaction solution, it was found that the trans isomer ratio was 49%.

Step 5: High Boiling Point Component Separation Step (2)

Furthermore, the above-described flask was charged with 175 parts by mass of the filtrate obtained in the cyanation step of step 1 of Example 1, and the mixture was heated at a pressure of 4 kPa, a condenser refrigerant temperature of (column top temperature) 140° C., and a flask internal temperature (column bottom temperature) of 190 to 230° C. The condensate was distilled with a gas cooling device to 81 mass % relative to the charged amount (flask residence time (residence time at the column bottom) 4 hours), thereby producing a distillate.

As a result of analysis on the distillate, it was found that the 1,4-dicyanocyclohexane yield was 89.0% relative to the charged amount, and its trans isomer ratio was 54%. The tank bottom had a 1,4-dicyanocyclohexane concentration of 49.5 mass % and a trans isomer ratio of 46%.

Step 6: Trans Isomer Separation Step (2)

A 500 mL flask equipped with a stirrer, a thermometer, a gas discharge pipe, and a packed column (packing: Sulzer pack, theoretical plate number: 10) equipped with a reflux device was charged with 280 parts by mass of the distillate produced in the trans-isomerization step of the above-described step 4, and distilled to 45 mass % relative to the charged amount (flask residence time (residence time at the column bottom) 5 hours) with the conditions of the following: a column top pressure of 6.7 kPa, a column top condenser refrigerant temperature (column top temperature) of 140° C., a flask internal temperature (column bottom temperature) of 230° C., and a reflux ratio of 1, thereby producing fractions.

As a result of analysis on the fractions, it was found that a total of 1,4-dicyanocyclohexane having a trans isomer ratio of 90% or more was 41.5 mass % relative to the charged amount, the 1,4-dicyanocyclohexane yield was 45.2%, and the average trans isomer ratio was 92%. The tank bottom had a trans isomer ratio of 32%.

Step 7: Aminomethylation Step

A filtrate containing 1,4-bis(aminomethyl)cyclohexane was produced in the same manner as in aminomethylation step of step 7 of Example 1 using the fraction produced as described above.

The filtrate was analyzed, and it was found that the 1,4-dicyanocyclohexane conversion rate was 100%, the 1,4-bis(aminomethyl)cyclohexane yield was 96%, and its trans isomer ratio was 86%.

The reaction solution was subjected to distillation under reduced pressure at 1.3 kPa, thereby producing a 97% yield of 1,4-bis(aminomethyl)cyclohexane having a purity of 99.5% or more and a trans isomer ratio of 85%.

Example 4

Steps 2 to 6: High Boiling Point Component Separation Step+Trans Isomer Separation Step+Trans-Isomerization Step A 500 mL flask equipped with a stirrer, a thermometer, a gas discharge pipe, and a packed column (packing: Sulzer pack, theoretical plate number: 10) equipped with a reflux device was charged with 330 parts by mass of the filtrate obtained in the cyanation step of step 1 of the above-described Example 1, and the filtrate was distilled to 80 mass % relative to the charged amount (flask residence time (residence time at the column bottom) 8 hours) with the following conditions: a column top pressure of 25 kPa, a column top condenser refrigerant temperature (column top temperature) of 140° C., a flask internal temperature (column bottom temperature) of 260 to 280° C., and a reflux ratio of 3, thereby producing fractions.

As a result of analysis on the fractions, it was found that a total of 1,4-dicyanocyclohexane having a trans isomer ratio of 90% or more was 71.1 mass % relative to the charged amount, the 1,4-dicyanocyclohexane yield was 84.6%, and the average trans isomer ratio was 94%. The tank bottom had a trans isomer ratio of 46%.

Step 7: Aminomethylation Step

A 1 L stainless steel reactor equipped with a stirrer, a thermometer, and a gas inlet tube was charged with 140 parts by mass of the produced 1,4-dicyanocyclohexane as described above, 14 parts by mass of a catalyst (manufactured by Kawaken Fine Chemicals Co., Ltd. manganese-containing Raney cobalt), 156 mL of 28 mass % ammonia water, and 292 mL of 1-butanol, and the mixture was heated to 80° C. while stirring at 400 rpm under normal pressure. Thereafter, hydrogen was fed intermittently so that the pressure was 0.95 MPa, and allowed reaction until there is no hydrogen absorption. After the termination of the reaction, the reaction product was cooled to room temperature, and the catalyst was removed by filtration.

The filtrate was analyzed, and it was found that the 1,4-dicyanocyclohexane conversion rate was 100%, the 1,4-bis(aminomethyl)cyclohexane yield was 96%, and its trans isomer ratio was 90%.

The reaction solution was subjected to distillation under reduced pressure at 1.3 kPa, thereby producing a 97% yield of 1,4-bis(aminomethyl)cyclohexane having a purity of 99.5% or more and a trans isomer ratio of 88%.

Step 8: Isocyanization Step

A 1.5 L stainless steel reactor equipped with a stirrer, a thermometer, a nitrogen inlet tube, a chlorine gas inlet tube, a phosgene inlet tube, a gas discharge pipe, a gas cooling device, and an automatic pressure regulating valve was charged with 55 parts by mass of 1,4-bis(aminomethyl)cyclohexane obtained in the above-described aminomethylation step, and 700 parts by mass of orthodichlorobenzene, and the mixture was heated to 60° C. while stirring at 300 rpm. Thereafter, 1.2 mol of hydrochloric acid gas was introduced at a flow rate of 0.15 L/min. Cold water was allowed to go through the reactor jacket, so that the internal temperature was kept to about 60 to 100° C.

Then, 77 parts by mass of phosgene was added thereto, and the pressure was increased to 0.2 MPa while the temperature of the reaction solution was increased to 150° C., and the reaction was further performed for 6 hours under a pressure of 0.2 MPa, a reaction temperature of 150° C. while adding phosgene. The phosgene added during the reaction was 230 parts by mass.

After the termination of the reaction, nitrogen gas was allowed to pass through at 100 to 150° C. at 0.4 L/min to degass. The solvent orthodichlorobenzene was distilled off under reduced pressure, and further distillation was performed under reduced pressure, thereby producing a 91% yield of 1,4-bis(isocyanatomethyl)cyclohexane having a purity of 99.5% or more and a trans isomer ratio of 87%.

Comparative Example 1

Step 4: Trans-Isomerization Step

A 500 mL flask equipped with a stirrer, a thermometer, a gas discharge pipe, and a gas cooling device was charged with 175 parts by mass of the tank bottom produced in trans isomer separation step (1) of step 3 of the above-described Example 1, and heated at 320° C. for 50 hours without adding the tank bottom produced in the high boiling point component separation step (1) of step 2 of Example 1. As a result of analysis on the reaction solution, it was found that the trans isomer ratio was 27%, and no drastic changes in the trans isomer ratio was observed.

Example 5

A reactor equipped with a stirrer, a thermometer, a nitrogen gas inlet tube, and a Dimroth condenser tube was charged with, 338.11 parts by mass of 1,4-bis(isocyanatomethyl)cyclohexane having a trans isomer ratio of 86% produced in Example 1 and 32.38 parts by mass of dodecylalcohol under a nitrogen gas atmosphere, and the temperature was increased to 85° C., thereby allowing reaction at the temperature for 4 hours.

Thereafter, the temperature was increased to 90° C., 0.007 parts by mass of bismuth octylate was added as a catalyst to allow reaction for 1 hour at that temperature, and the temperature was increased to 100° C. Reaction was allowed at that temperature for 4 hours, and thereafter, FT-IR and NCO mass % measurements were carried out to check the isocyanate group concentration.

Thereafter, 0.01 parts by mass of bismuth octylate was added thereto, and thereafter, the reaction was continued for 20 hours finally at 100° C. Thereafter, 0.02 parts by mass of o-toluene sulfonamide was added, and the reaction was terminated.

The produced reaction solution was treated with a thin film evaporator, thereby removing unreacted 1,4-bis(isocyanatomethyl)cyclohexane, and producing a light yellow transparent polyisocyanate composition. The polyisocyanate composition was subjected to NMR, FT-IR, and GPC measurements, and it was found that the allophanate/isocyanurate composition ratio was 82/18, and the urethane group was not observed substantially.

Furthermore, the unreacted 1,4-bis(isocyanatomethyl)cyclohexane content was 0.5 mass %, and the NCO mass % was 13.6%. Dilution with 1000% or more of ethyl acetate caused no cloudiness, showing complete dissolution.

Example 6

The polyisocyanate composition produced in Example 5 was blended with a commercially available acrylic polyol (manufactured by DIC, trade name: ACRYDIC A-801) so that the equivalent ratio of isocyanate group/hydroxyl group was 1.0.

Thereafter, the produced liquid mixture was applied on a steel plate treated with chromate and a glass plate to give an average film thickness of 25±5 μm. The applied liquid mixture was cured at 25° C. and a relative humidity of 55%.

As a result, a polyurethane resin having a Set-to-Touch Time of 3.5 minutes, a Dry Hard Time of 4.8 hours, a Coating Hardness of H, a shock resistance of 50 cm, an Erichsen of 8 mm, and a tensile strength of 73 MPa was produced.

The polyurethane resin was evaluated as follows.
<Evaluation>
<Set-to-Touch Time (Unit: Minute)>

In conformity with JIS K 5600-1-1, the center of a coated surface was touched by a finger under the conditions of 25° C. and 55% relative humidity and, when none of the sample was transferred to the fingertip, the set-to-touch time was determined.
<Dry Hard Time (Unit: Hour)>

In conformity with JIS K 5600-1-1, the center of the test piece was strongly pinched between the thumb and forefinger under the conditions of 25° C. and 55% relative humidity, and when no fingerprint impression was left on the coated surface to be in a dry-hard state, the dry hard time was determined.
<Coating Hardness>

In conformity with JIS-K 5600-5-6, the pencil hardness at the time when a surface of the coating film was scratched was evaluated as coating hardness.
<Shock Resistance (unit: cm)>

In conformity with JIS K 56005-6, shock resistance (cm) was evaluated by placing a center punch having a ½ inch diameter on the coated surface, dropping a 500 g-weight object, and measuring (cm) a height where the coating was broken.
<Erichsen (mm)>

In conformity with JIS K 5600-5-6, Erichsen (mm) was evaluated by placing a center punch having an ½ inch diameter on the coating surface, fixing firmly the surroundings of the coated place, and measuring the length (mm) where the coated surface cracked when the punch was pushed at a predetermined speed relative to the coated plate.
<Tensile Strength (Unit: MPa)>

Tensile strength was measured using a tensile and compression testing machine (manufactured by INTESCO co., Ltd., Model205N) by removing the sample from the glass plate, and testing with a tensile speed of 300 mm/min after drying at 23° C.

Example 7

To a four-neck flask quipped with a stirrer, a thermometer, a reflux pipe, and a nitrogen inlet tube, 253.2 parts by mass of 1,4-bis(isocyanatomethyl)cyclohexane produced in Example 1 and 0.025 parts by mass of additive (trade name: JP-310, manufactured by Johoku Chemical Co. Ltd.) were added and dissolved.

Then, 646.5 parts by mass of polyethylene glycol (trade name: PEG-2000U, manufactured by NOF Corporation) having number average molecular weight of 2000 was introduced thereto, and allowed to react in a nitrogen atmosphere at 80° C. for 4 hours, thereby producing isocyanate group-terminated polyurethane prepolymer.

After the produced prepolymer was adjusted to 80° C. 9.92 parts by mass of a heat-resistant stabilizer (trade name: SUMILIZER GA-80, manufactured by Sumitomo Chemical Co., Ltd.), and 0.05 parts by mass of a solution in which a catalyst (trade name: U-600 (octanoic acid bismuth), manufactured by Nitto Chemical Industry Co. Ltd.) was diluted with diisononyl adipate (trade name: DINA, manufactured by J-PLUS Co., Ltd.) to be 4 mass %, were added thereto.

Then, 2.95 parts by mass of stabilizer 1 (trade name: TINUVIN 234, manufactured by BASF) and 2.95 parts by mass of stabilizer 2 (trade name: ADK STAB LA-72, manufactured by ADEKA CORPORATION) were added thereto, and the mixture was stirred and mixed at 600 rpm for about 2 minutes until dissolved using a three one motor.

Thereafter, 84.2 parts by mass of 1,4-butanediol (manufactured by Mitsubishi chemical corporation) adjusted to 80° C. in advance was added as a chain extender, and further stirred sufficiently for about 8 minutes until the whole is homogenous. Thereafter, the reaction liquid mixture was introduced to a Teflon coated vessel, and allowed to react in a nitrogen atmosphere at 150° C. for 1 hour, and thereafter, continuously, allowed to react at 100° C. for 23 hours, thereby producing a polyurethane resin.

Thereafter, polyurethane resin bulks were taken out from the vessel, and ground with a grinder, and then thereafter pellets were produced continuously using a uniaxial extruder having a barrel with a temperature adjusted in the range of 205 to 225° C.

Then, after drying in a nitrogen atmosphere at 80° C. for 24 hours, an injection mold device is used to produce a 20 cm×20 cm injection sheet having a thickness of 2 mm. The sheet was aged for 7 days under conditions of constant temperature and constant humidity at 23° C. and a relative humidity of 50%.

The produced sheet was measured for JIS-A hardness and tensile strength in conformity with "JIS K-7311 Testing methods for thermoplastic polyurethane elastomers": the hardness was 90, and the tensile strength was 42 MPa.

Meanwhile, the produced pellets were dried in a nitrogen atmosphere at 80° C. for 24 hours, and thereafter, extrusion molded with a uniaxial extruder having T-dice at a screw number of revolution of 20 rpm and in the range of a cylinder temperature of 200 to 250° C., thereby producing a film having a thickness of 20 μm. Thereafter, the produced film (thickness 20 μm) was aged for 7 days under conditions of constant temperature and constant humidity at a room temperature of 23° C. and a relative humidity of 50%.

The film had a softening temperature of 176° C., a water vapor permeability based on A-1 method of 6500 (g/m$^2$·24 h), and a water vapor permeability based on B-1 method of 114100 (g/m$^2$·24 h) in conformity with JIS L-1099.

Furthermore, as a result of measuring the tensile strength in conformity with "JIS K-7311 Testing methods for thermoplastic polyurethane elastomers", it was found that 100% modulus was 7.9 MPa, the tensile strength was 42 MPa, and the elongation at break was 680%.

The polyurethane resin was evaluated as follows.
<Evaluation>
<Softening Temperature (Unit:° C.)>

The softening temperature of a polyurethane elastomer film having a 20 μm thickness was measured using a thermomechanical analyzer (manufactured by Seiko Instruments, model: TMA/6600) in conformity with the method described in JIS K7196.

<Water Vapor Permeability of Film (Unit: $(g/m^2 \cdot 24\ h)$)>

Water vapor permeability was measured in conformity with A-1 method (calcium chloride method) and B-1 method (potassium acetate) of JIS L-1099. In B-1 method, measurement was performed after placing a nylon taffeta on the place where film makes contact with water. Thereafter, the values were calculated based on 24 hours.

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

The method for producing trans-bis(aminomethyl)cyclohexane, the method for producing bis(isocyanatomethyl)cyclohexane, the bis(isocyanatomethyl)cyclohexane, and the polyisocyanate composition of the present invention are useful for a polyurethane resin material and for a production method thereof, and the polyurethane resin of the present invention can be used in wide range in various industrial fields.

DESCRIPTION OF REFERENCE NUMERAL

1 Plant
3 Cyanation unit
5 High boiling point component separation unit
6 Trans isomer separation unit
7 Isomerization unit (into trans)
8 Aminomethylation unit

The invention claimed is:

1. A method for producing trans-bis(aminomethyl)cyclohexane, the method including the steps of:
   a high boiling point component separation step in which a high boiling point component is separated by distillation from a mixture containing dicyanocyclohexane and the high boiling point component, wherein the dicyanocyclohexane comprises a mixture of trans-dicyanocyclohexane and cis-dicyanocyclohexane, and wherein the high boiling point component is taken out as a tar component from a column bottom of a distillation column,
   a trans isomer separation step in which trans-dicyanocyclohexane is separated from the mixture,
   a trans-isomerization step in which the tar component is supplied to remaining cis-dicyanocyclohexane in the mixture, and the remaining cis-dicyanocyclohexane is isomerized into trans-dicyanocyclohexane by heating the remaining cis-dicyanocyclohexane in the presence of the tar component, and
   an aminomethylation step in which trans-dicyanocyclohexane produced by the trans isomer separation step and the trans-isomerization step is allowed to contact with hydrogen to produce trans-bis(aminomethyl)cyclohexane.

2. The method for producing trans-bis(aminomethyl)cyclohexane according to claim 1, wherein in the trans-isomerization step, 2 to 30 parts by mass of the tar component is present relative to 100 parts by mass of the dicyanocyclohexane.

3. The method for producing trans-bis(aminomethyl)cyclohexane according to claim 1, wherein:
   the high boiling point component separation step, the trans isomer separation step, and the trans-isomerization step are performed using a single distillation column,
   trans-dicyanocyclohexane is taken out from a column top of the distillation column, and the tar component is taken out from a column bottom of the distillation column, and
   the tar component that is taken out is added back into the distillation column.

4. The method for producing trans-bis(aminomethyl)cyclohexane according to claim 3, wherein the distillation column has
   a column top temperature of 140° C. or more and 220° C. or less,
   a column bottom temperature of 200° C. or more and 320° C. or less, and
   the residence time at the column bottom is 1 hour or more and 50 hours or less.

5. A method for producing bis(isocyanatomethyl)cyclohexane, comprising:
   a step of producing trans-bis(aminomethyl)cyclohexane by a process including:
      a high boiling point component separation step in which a high boiling point component is separated by distillation from a mixture containing dicyanocyclohexane and the high boiling point component, wherein the dicyanocyclohexane comprises a mixture of trans-dicyanocyclohexane and cis-dicyanocyclohexane, and wherein the high boiling point component is taken out as a tar component from a column bottom of a distillation column,
      a trans isomer separation step in which trans-dicyanocyclohexane is separated from the mixture,
      a trans-isomerization step in which the tar component is supplied to remaining cis-dicyanocyclohexane from the mixture, and the remaining cis-dicyanocyclohexane is isomerized into trans-dicyanocyclohexane by heating the remaining cis-dicyanocyclohexane in the presence of the tar component, and
      an aminomethylation step in which trans-dicyanocyclohexane produced by the trans isomer separation step and the trans-isomerization step is allowed to contact with hydrogen to produce trans-bis(aminomethyl)cyclohexane, and
   a step of producing bis(isocyanatomethyl)cyclohexane by isocyanizing the obtained trans-bis(aminomethyl)cyclohexane.

6. A method for producing a polyisocyanate composition comprising:
   a step of producing trans-bis(aminomethyl)cyclohexane by a process including:
      a high boiling point component separation step in which a high boiling point component is separated by distillation from a mixture containing dicyanocyclohexane and the high boiling point component, wherein the dicyanocyclohexane comprises a mixture of trans-dicyanocyclohexane and cis-dicyanocyclohexane, and wherein the high boiling point component is taken out as a tar component from a column bottom of a distillation column, a trans isomer separation step in which trans-dicyanocyclohexane is separated from the mixture, a trans-isomerization step in which the tar component is supplied to remaining cis-dicyanocyclohexane in the mixture, and the remaining cis-dicyanocyclohexane is isomerized into trans-dicyanocyclohexane by heating the dicyanocyclohexane the remaining cis-dicyanocyclohexane in the presence of the tar component, and an aminomethylation step in which trans-dicyanocyclohexane produced by the trans isomer separation step and the trans-isomerization step is allowed to contact with hydrogen to produce trans-bis(aminomethyl)cyclohexane, a step of producing bis(isocyanatomethyl)cyclohexane by isocyanizing the obtained trans-bis(aminomethyl)cyclohexane, and a step of modifying the obtained bis(isocyanatomethyl)cyclohexane to produce a polyisocyanate composition containing at least one functional group of (a) to (e) below:
(a) an isocyanurate group,
(b) an allophanate group,
(c) a biuret group,
(d) a urethane group, and
(e) a urea group.

7. A method for producing a polyurethane resin comprising:
a step of producing trans-bis(aminomethyl)cyclohexane by a process including:
a high boiling point component separation step in which a high boiling point component is separated by distillation from a mixture containing dicyanocyclohexane and the high boiling point component, wherein the dicyanocyclohexane comprises a mixture of trans-dicyanocyclohexane and cis-dicyanocyclohexane, and wherein the high boiling point component is taken out as a tar component from a column bottom of a distillation column, a trans isomer separation step in which trans-dicyanocyclohexane is separated from the mixture, a trans-isomerization step in which the tar component is supplied to the remaining cis-dicyanocyclohexane in the mixture, and the remaining cis-dicyanocyclohexane is isomerized into trans-dicyanocyclohexane by heating the remaining cis-dicyanocyclohexane in the presence of the tar component, and aminomethylation step in which trans-dicyanocyclohexane produced by the trans isomer separation step and the trans-isomerization step is allowed to contact with hydrogen to produce trans-bis(aminomethyl)cyclohexane, a step of producing bis(isocyanatomethyl)cyclohexane by isocyanizing the obtained trans-bis(aminomethyl)cyclohexane, and a step of producing a polyurethane resin by allowing the obtained bis(isocyanatomethyl)cyclohexane to react with an active hydrogen compound.

8. A method for producing a polyurethane resin, comprising:
a step of producing trans-bis(aminomethyl)cyclohexane by a process including:
a high boiling point component separation step in which a high boiling point component is separated by distillation from a mixture containing dicyanocyclohexane and the high boiling point component, wherein the dicyanocyclohexane comprises a mixture of trans-dicyanocyclohexane and cis-dicyanocyclohexane, and wherein the high boiling point component is taken out as a tar component from a column bottom of a distillation column, a trans isomer separation step in which trans-dicyanocyclohexane is separated from the mixture, a trans-isomerization step in which the tar component is supplied to remaining cis-dicyanocyclohexane in the mixture, and the remaining cis-dicyanocyclohexane is isomerized into trans-dicyanocyclohexane by heating the remaining cis-dicyanocyclohexane in the presence of the tar component, and an aminomethylation step in which trans-dicyanocyclohexane produced by the trans isomer separation step and the trans-isomerization step is allowed to contact with hydrogen to produce trans-bis(aminomethyl)cyclohexane, a step of producing bis(isocyanatomethyl)cyclohexane by isocyanizing the obtained trans-bis(aminomethyl)cyclohexane, a step of modifying the obtained bis(isocyanatomethyl)cyclohexane to produce a polyisocyanate composition containing at least one functional group of (a) to (e) below:
(a) an isocyanurate group,
(b) an allophanate group,
(c) a biuret group,
(d) a urethane group, and
(e) a urea group, and a step of producing a polyurethane resin by allowing the obtained bis(isocyanatomethyl)cyclohexane to react with an active hydrogen compound.

* * * * *